US008343238B1

(12) United States Patent
Lopez et al.

(10) Patent No.: US 8,343,238 B1
(45) Date of Patent: Jan. 1, 2013

(54) PROCESS FOR ALTERING THE APPEARANCE OF HAIR USING A COMPOSITION CONTAINING DYES AND NON-HYDROXIDE BASES

(75) Inventors: Gloria Lopez, Fairview, NJ (US); Jeremy Puco, Budd Lake, NJ (US)

(73) Assignee: L'Oreal SA.

( * ) Notice: Subject to any disclaimer, the term of this patent is extended or adjusted under 35 U.S.C. 154(b) by 0 days.

(21) Appl. No.: 13/341,473

(22) Filed: Dec. 30, 2011

(51) Int. Cl.
*A61Q 5/10* (2006.01)
(52) U.S. Cl. ............. 8/405; 8/408; 8/431; 8/552; 8/581; 8/585; 8/597; 8/604; 132/202; 132/208
(58) Field of Classification Search .............. 8/405, 408, 8/431, 552, 581, 585, 597, 604; 132/202, 132/208
See application file for complete search history.

(56) References Cited

U.S. PATENT DOCUMENTS

| | | | |
|---|---|---|---|
| 4,507,278 A | 3/1985 | DeMarco et al. | |
| 4,698,065 A | 10/1987 | Hoeffkes et al. | |
| 4,844,711 A | 7/1989 | Hoppe et al. | |
| 5,160,730 A | 11/1992 | Dubief | |
| 5,180,584 A | 1/1993 | Sebag | |
| 5,275,755 A | 1/1994 | Sebag | |
| 5,637,306 A | 6/1997 | Cauwet | |
| 5,766,576 A | 6/1998 | Lowe et al. | |
| 5,879,414 A | 3/1999 | Milazzo | |
| 6,306,182 B1 | 10/2001 | Chan et al. | |
| 6,338,741 B1 | 1/2002 | Vidal et al. | |
| 6,352,699 B1 | 3/2002 | Mondet et al. | |
| 6,368,584 B1 | 4/2002 | Garnier | |
| 6,551,361 B1 | 4/2003 | Cornwell et al. | |
| 6,607,713 B1 | 8/2003 | Chodorowski et al. | |
| 6,645,258 B2 | 11/2003 | Vidal et al. | |
| 6,953,572 B1 | 10/2005 | Samain | |
| 6,953,584 B1 | 10/2005 | Samain | |
| 7,037,347 B2 | 5/2006 | Kuzuhara et al. | |
| 7,122,062 B2 | 10/2006 | Yamashita et al. | |
| 7,176,170 B2 | 2/2007 | Dubief | |
| 7,223,384 B1 | 5/2007 | Decoster | |
| 7,244,420 B1 | 7/2007 | Samain | |
| 7,740,664 B2 | 6/2010 | Benabdillah | |
| 7,799,093 B2 | 9/2010 | Brun et al. | |
| 7,879,113 B2 | 2/2011 | Simonet et al. | |
| 7,901,464 B2 | 3/2011 | Hercouet et al. | |
| 7,905,927 B2 | 3/2011 | Hercouet | |
| 7,909,889 B2 | 3/2011 | Charrier et al. | |
| 7,909,892 B2 | 3/2011 | Lautenbach et al. | |
| 7,959,687 B2 | 6/2011 | Charrier et al. | |
| 2002/0041856 A1 | 4/2002 | Jeanne-Rose et al. | |
| 2004/0013632 A1 | 1/2004 | Giroud et al. | |
| 2004/0045099 A1 | 3/2004 | Kuzuhara et al. | |
| 2004/0185020 A1 | 9/2004 | Gawtrey | |
| 2005/0071932 A1 | 4/2005 | Lautenbach et al. | |
| 2005/0100523 A1 | 5/2005 | Maubru | |
| 2008/0226576 A1 | 9/2008 | Benabdillah | |
| 2009/0183320 A1 | 7/2009 | Benabdillah | |
| 2009/0291058 A1 | 11/2009 | Woodland | |
| 2009/0293899 A1 | 12/2009 | Woodland | |
| 2010/0254932 A1 | 10/2010 | Benabdillah | |
| 2010/0297049 A1 | 11/2010 | Samain et al. | |
| 2011/0052520 A1 | 3/2011 | Nguyen et al. | |
| 2011/0158927 A1 | 6/2011 | Viravau | |

FOREIGN PATENT DOCUMENTS

| | | |
|---|---|---|
| CN | 101069673 A | 11/2007 |
| CN | 101069673 A | 11/2007 |
| DE | 2359399 | 6/1973 |
| DE | 1486576 | 9/1977 |
| DE | 3843892 A1 | 2/1990 |
| DE | 4133957 A1 | 4/1993 |
| DE | 19543988 A1 | 5/1997 |
| DE | 102006026009 A1 | 12/2007 |
| EP | 0560682 | 9/1993 |
| EP | 898958 A1 | 3/1999 |
| EP | 898960 A1 | 3/1999 |
| EP | 1216022 A1 | 6/2002 |
| EP | 1216023 A1 | 6/2002 |
| EP | 1221929 A1 | 7/2002 |
| EP | 1510197 A1 | 3/2005 |
| EP | 1862198 A2 | 12/2007 |
| EP | 1889602 | 2/2008 |
| EP | 1944062 | 7/2008 |
| FR | 733.749 | 2/1932 |
| FR | 2633940 A1 | 1/1990 |
| FR | 2750048 A1 | 12/1997 |
| FR | 2789896 A1 | 8/2000 |
| FR | 1207842 A1 | 5/2002 |
| FR | 2836633 A1 | 9/2003 |
| FR | 2838960 A1 | 10/2003 |

(Continued)

OTHER PUBLICATIONS

"Chemistry and Technology of Silicones" (1968), Academic Press.
"Volatile Silicone Fluids for Cosmetics" (Jan. 1976,vol. 1, pp. 29-32), Cosmetics and Toiletries.
"Industrial Polysaccharides" (vol. 61, No. 7, p. 1315-1322, 1989), Pure & Appl. Chem.
U.S. Appl. No. 61/581,906, filed Dec. 30, 2011, Gloria Lopez et al.

*Primary Examiner* — Eisa Elhilo

(74) *Attorney, Agent, or Firm* — L'Oreal USA

(57) ABSTRACT

A process for altering the appearance of hair, the process comprising the steps of (a) providing a composition for dyeing and reducing curl and/or frizziness of hair, said composition comprising, in a cosmetically acceptable carrier: (i) at least one non-hydroxide base; (ii) at least one protein denaturant different from (a)(i); (iii) at least one dye chosen from oxidative dye precursors; (iv) at least one thickening agent; (v) optionally, at least one alkoxysilane comprising at least one solubilizing functional group; and (vi) optionally, at least one fatty substance; (b) contacting the hair with the composition in (a) to form treated hair; (c) smoothing the treated hair using a combination of heat and means for physically smoothing hair to form smoothed hair; (d) optionally, shampooing the smoothed hair; and (e) rinsing the smoothed hair.

45 Claims, No Drawings

FOREIGN PATENT DOCUMENTS

| | | |
|---|---|---|
| FR | 2910276 | 6/2008 |
| FR | 2922759 A1 | 5/2009 |
| FR | 2926984 | 8/2009 |
| FR | 2929112 A1 | 10/2009 |
| FR | 2944963 A1 | 11/2010 |
| FR | 2944964 A1 | 11/2010 |
| FR | 2944966 A1 | 11/2010 |
| FR | 2950531 | 4/2011 |
| GB | 1026978 | 4/1966 |
| GB | 1153196 | 5/1969 |
| JP | 60004116 A | 1/1985 |
| JP | 02019576 A | 1/1990 |
| JP | 7330556 A | 12/1995 |
| JP | 9110659 | 4/1997 |
| JP | 9175960 A | 7/1997 |
| JP | 9278636 A | 10/1997 |
| JP | 9278636 A | 10/1997 |
| JP | 2001220322 A | 8/2001 |
| JP | 3686352 B2 | 11/2002 |
| JP | 2002326916 A | 11/2002 |
| JP | 2003128527 A | 5/2003 |
| JP | 2004217672 A | 8/2004 |
| JP | 2008273869 A | 11/2008 |
| WO | WO 94/08969 | 4/1994 |
| WO | WO 94/08970 | 4/1994 |
| WO | WO 96/15765 | 5/1996 |
| WO | WO 99/60993 | 12/1999 |
| WO | WO 0048557 | 8/2000 |
| WO | WO 2006/018198 A1 | 2/2006 |
| WO | WO 2008/020730 A1 | 2/2008 |
| WO | WO 2010023559 A2 * | 3/2010 |
| WO | WO 2011/052520 A1 | 5/2011 |
| WO | WO 2011/073279 | 6/2011 |
| WO | WO 2011/073578 | 6/2011 |
| WO | WO2011/074144 | 6/2011 |
| WO | WO 2011073578 A2 | 6/2011 |
| WO | WO2011/089985 | 7/2011 |
| WO | WO 2011/089985 | 7/2011 |

* cited by examiner

PROCESS FOR ALTERING THE APPEARANCE OF HAIR USING A COMPOSITION CONTAINING DYES AND NON-HYDROXIDE BASES

FIELD OF THE INVENTION

The present invention is directed to a novel process and composition for dyeing hair while reducing the curl pattern and/or frizziness of the hair.

BACKGROUND OF THE INVENTION

Chemical treatments on human hair such as relaxers, straighteners, waves, perms, oxidative and direct dyes, highlights, lightening compositions and bleaches are much sought after by consumers. Such chemical treatments employ various reducing and oxidizing agents, alkalizing agents, and coloring agents that help re-shape, artificially color, decolorize, modify the color shade/tone or enhance the appearance and color of hair.

However, such chemical treatments and the various ingredients employed in these treatments are generally known to result in hair breakage and loss, dryness, roughness and brittleness, and skin and/or scalp irritation. Often times, these chemical treatments are used with the application of heat and mechanical combing or brushing which may cause more damage to the hair.

One example of a chemical treatment that may adversely affect the quality of hair fibers are conventional permanent hair dyeing products which use the combination of compositions containing oxidative dye precursors, also known as primary intermediates or oxidation bases, and oxidizing products containing oxidizing agents such as hydrogen peroxide. Hair dyeing compositions typically contain aqueous ammonia as an alkalizing agent and for activating the oxidizing agent. These alkalizing agents also cause the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. However, the use of ammonia may affect the user, not only because of the undesirable odor of ammonia, but because it may also pose greater risks of intolerance, for instance, irritation of the scalp and stinging.

Chemical treatments products for shaping or changing the shape and configuration of hair include hair straightening or relaxing products which are generally composed of a strong hydroxide base compound, typically, an alkaline metal hydroxide, that breaks the bonds in the hair in order to straighten or relax curly/kinky hair. These products are usually applied quickly and can only remain in the hair for a very limited amount of time because the alkalinity of such products, if not rinsed from the hair at the appropriate time, can damage the hair, as well as cause chemical burns to the scalp and areas surrounding the hair.

Other straightening or relaxing formulations use guanidinium hydroxide which can be formed from the reaction of guanidine carbonate and a soluble hydroxide such as calcium hydroxide. While such a system may provide a better relaxing efficacy and better skin tolerance, the reaction also forms calcium carbonate which makes the final rinsing of the hair much more difficult, and leaves on the hair and the scalp, mineral particles that give the hair a coarse feel and an unattractive appearance resembling dandruff.

Hair straighteners or reshaping technology can also employ reducing agents such as thighlycolic acid and cysteine compounds or non-thiol-based reducing agents such as sulfites and bisulfites which permanently reduce hair bonds or protein denaturants in combination with heat.

Other straightening products contain formalin or formalin derivatives, which are known to break down to formaldehyde with high heat, such as during flat ironing of the hair. One major drawback is the generation of formaldehyde fumes which have been found to cause headaches, respiratory, eye, and mucous membrane irritations, respiratory illnesses, cancer, or even death.

Thus, in view of the potential irritation to the skin or scarp, and the potential damage to hair caused by available chemical treatments, successive chemical treatments of the hair within a short period of time, i.e., a few hours, is generally not recommended. More particularly, conventional and customary practice by consumers and hair dressers is to have a waiting period of at least 24 hours, preferably, a few days, in between two or more different chemical hair treatments. Such practices may also help minimize other types of problems which may arise from successively chemically treating the hair as a result of undesired reactions between successive different chemical treatments.

An example of a hair treatment process that may result in the problems described above may consist of a hair straightening or relaxing process that is immediately followed by a conventional oxidative hair color that employs hydrogen peroxide. Such a process can result in a significant decrease in the quality of the hair fibers, leading to increased roughness and damage to the hair and/or prevent the hair's color or shade from being lightened, bleached, dyed or altered correctly after the chemical treatment.

Successive chemical treatments of the hair can also be inconvenient to the consumer who has to spend a lot of time going through two different treatments, wait in between treatments and return to the hair dresser for the second treatment.

Thus, there exists a need to improve existing methods, compositions and hair treatment regimens or systems that allow the consumer to effectively change the appearance, that is, the color and/or shape of their hair in a convenient, efficient and safe manner, while minimizing the damage to the hair and other adverse effects and disadvantages to the consumer. There is also a need for processes and/or compositions which can take the place of successive chemical treatments.

For example, it would be desirable to oxidatively dye hair and chemically shape or straighten the hair at the same time. However, this may require introducing other ingredients into hair coloring compositions which may affect the suspension and/or solubility of the dye compounds in the dye composition, the hair-lightening properties of the dye composition, the rheology or viscosity of the dye composition, and the dye application properties. Thus, the selection of ingredients presents an even greater challenge to the manufacturers of hair treatment products because the composition/process not only has to remain effective, it also has to remain safe to use and not cause more irritation to the skin and scalp.

Thus, there is still an ongoing need and desire to provide a composition and process for effectively coloring and/or lightening the color of hair such as achieving chromaticity of the color and homogeneity of the coloration along the hair fiber in a manner that is efficient, yet safe and minimizes damage to the hair fiber. At the same time, it is highly desirable that these composition and process are able to impart other cosmetic and functional benefits to the hair such as curl and frizz reduction, greater and longer lasting curl pattern, increased manageability of hair and fiber strength and less hair treatment or processing times to achieve these attributes.

BRIEF SUMMARY OF THE INVENTION

The present invention is directed to a process for altering the appearance of hair, the process comprising the steps of:
  (a) providing a composition for dyeing and reducing curl and/or frizziness of hair, said composition, in a cosmetically acceptable carrier:
    (i) at least one non-hydroxide base;
    (ii) at least one protein denaturant different from (a)(i);
    (iii) at least one dye chosen from oxidative dye precursors;
    (iv) at least one thickening agent;
    (v) optionally, at least one alkoxysilane comprising at least one solubilizing functional group; and
    (vi) optionally, at least one fatty substance;
  (b) contacting the hair with the composition in (a) to form treated hair;
  (c) smoothing the treated hair using a combination of heat and means for physically smoothing hair to form smoothed hair;
  (d) optionally, shampooing the smoothed hair; and
  (e) rinsing the smoothed hair.

The present invention is also directed to a composition for dyeing and reducing curl and/or frizziness of hair, said composition comprising, in a cosmetically acceptable carrier:
  (a) from about 1 to about 5% by weight of at least one non-hydroxide base chosen from monoethanolamine and triethanolamine;
  (b) from about 2 to about 20% by weight of by weight of a protein denaturant comprising urea and hydroxyethylurea present in a ratio by weight ranging from about 5:1 to about 2:1;
  (c) at least one dye chosen from oxidative dye precursors;
  (d) at least one thickening agent chosen from xanthan gum and guar gum;
  (e) at least one fatty substance in an amount of at least 10% by weight; and
  (f) from about 1 to about 10% by weight of at least one alkoxysilane comprising at least one solubilizing functional group;
wherein all weights are based on the weight of the composition.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

As used herein, the term "hair" is meant to include keratinous fibers. As used, the term "hair" may include "living" hair, i.e. on a living body, or may be "non-living" i.e. in a wig, hairpiece or other aggregation of non-living fibers, such as though used in textiles and fabrics. Mammalian hair, e.g. human hair, is preferred in various embodiments. However wool, fur and other melanin-containing fibers are suitable for use in the methods and with the compositions described herein.

The term "anhydrous" as used herein is intended to mean that the composition is either completely free of unbound water or contains substantially no unbound water, such as, for example, no more than about 1% by weight, such as no more than about 0.5% by weight, based on the weight of each composition.

As used herein, the phrase "salts and derivatives thereof" is intended to mean all salts and derivatives comprising the same functional structure as the compound they are referring to, and that have similar properties.

As used herein, the terms "pre-alkalizing" and "pre-alkalized" mean that the hair has a higher pH than when it has not been subjected to chemical treatment, as described herein.

As used herein, the phrase "minimizing damage" to the hair and/or skin is intended to mean that the breakage of the hair has been reduced or eliminated.

As used herein, the term "ready-to-use composition" means a composition intended to be applied in unmodified form to the keratin fibers, i.e. it may be stored in unmodified form before use or may result from the extemporaneous mixing of two or more compositions.

As used herein, the expression "altering the appearance of hair" means contacting the hair with at least one composition containing at least one chemical ingredient that changes or contributes to changing the shape and/or the color of the hair, to any degree.

As used herein, the term "applying" a composition to the hair or "treating" the hair with a composition is intended to mean contacting the hair with at least one of the compositions of the invention, in any manner.

As used herein, the terms "straightening" or "straighten" or "relaxing" or "relax" the hair mean to remove the curl from the hair or reduce the degree of curl of the hair for a period of time, permanently and/or temporarily. It also means changing the shape of hair or the degree of curl in the hair to make the hair more straight. It can also mean removing or reducing the frizziness of the hair.

As used herein, "cosmetically acceptable" means that the item in question is compatible with any human keratin material and in particular human keratinous fibers, such as human hair.

As used herein, "cosmetically acceptable carrier" means a carrier that is compatible with any human keratin material and in particular human keratinous fibers, such as human hair.

"Lifting" as used herein is defined as the process by which the natural hair melanin is removed which is typically achieved in an alkaline environment whereby the cuticles of the hair are opened to allow penetration of an oxidizing agent. Such an oxidizing agent breaks down the melanin by providing it with oxygen, and the melanin molecule is colorless when oxidized. This leaves the hair lightened from its natural color.

The term "composition for dyeing and reducing curl and/or frizziness of hair" as used herein refers to the hair curl and/or frizz recuding and dyeing composition as described in the present disclosure.

The term "suspending agent" as used herein refers to raw materials and ingredients which aid in homogeneously/uniformly dispersing other ingredients, such as dyeing agents, in the compositions of the present disclosure. Suspending agents are also employed in order to provide a suitable consistency or rheology and other cosmetic benefits to the compositions of the present disclosure and to hair, skin or scalp.

As used herein, "natural hair color" refers to the color of hair resulting from the melanin pigments present in the hair.

As used herein, "conditioning" means imparting to at least one keratinous fiber at least one property chosen, from combability, manageability, moisture-retentivity, luster, shine, and softness. In case of combing, the level of conditioning is evaluated by measuring, and comparing, the ease of combability of the treated hair and of the untreated hair in terms of combing work (gm-in).

As used herein, "formed from," means obtained from chemical reaction of, wherein "chemical reaction," includes spontaneous chemical reactions and induced chemical reactions. As used herein, the phrase "formed from", is open ended and does not limit the components of the composition to those listed.

As used herein, the term "rheology-modifying agent" or "rheology modifier" means any compound capable of giving a viscosity to the oxidizing composition such that, once it is applied onto hair, this composition does not run, and remains perfectly localized at the point of application.

As used herein, the term "aqueous ammonia" refers to ammonia derived from ammonium compounds which are added to a composition, such as ammonium hydroxide. Thus, the use of the term "ammonia" refers to aqueous ammonia.

As used herein, the methods and compositions disclosed may be used on the hair that has not been artificially dyed or pigmented.

As used herein, the methods and compositions disclosed may be also used on the hair that has been artificially dyed or pigmented.

The methods and compositions disclosed are also used to reduce the frizziness of hair and/or improve the condition of the hair or keep hair conditioned. When the amount of moisture in hair decreases due to weather conditions or exposure to high temperatures during styling processes, the hair gives up surface electrons more readily and develops a positive electrostatic charge. The positive charge of individual hair fibers causes the hair fibers to repel one another resulting in a "static flyaway" condition (i.e., frizzy hair). Loss of moisture in the hair also causes hair to become brittle and damaged resulting in less shiny and more unattractive hair. Hair is often exposed to dry weather conditions in arid regions and/or during the winter months. Furthermore, many styling processes utilize heat to drive out moisture in the hair in order to lock in a temporary style that persists until the hair reabsorbs moisture.

Alkoxysilanes are not typically used in formulating cosmetic products/personal care products. In particular, alkoxysilanes are not usually employed in hair products, including manageability products for reducing curl and frizz. However, alkoxysilanes, particularly those with at least one solubilizing functional group can attract water molecules, thereby causing a gelling effect when exposed to the water. Without intending to be bound by theory, the use of alkoxysilanes is believed to help with reducing the adverse effects of the use of heat on the hair which would tend to reduce the moisture of the hair, thereby resulting in unattractive and dry hair.

The present invention is based on the surprising and unexpected finding that the methods and compositions of the present disclosure resulted in significantly improved curl and frizz reducing capability and hair dyeing and/or lightening capability, thus, eliminating the need for two separate procedures and the long wait between the procedures.

It has been surprisingly found that by employing the methods and compositions of the present disclosure, the following several significant advantages can be realized, as compared to conventional methods of dyeing and straightening hair: shorter processing times; comparable color-fastness to conventional dyeing methods using oxidative developers; improved color deposit on the hair; little to no odor. In some instances, depending on the oxidative dye and/or coupler molecule used, different colors/shades may be obtained compared to the conventional hair coloring compositions/methods. It should also be noted that by varying the pH of the system, different levels of color vibrancy on hair can be achieved.

It was also surprisingly found that the curl/frizz reduction and the color retention capabilities as provided by the present disclosure are long lasting and comparable to, if not better than the results provided by commercial products and may last for several Weeks such as from about 4 weeks to about 8 weeks.

Without intending to be bound by theory, it is believed that the present invention's composition for dyeing and reducing curl and/or frizziness of hair results in a unique synergy between the non-hydroxide base, the two protein denaturants, and the thickening agent. This believed synergy translates to a composition that provides overall improved dyeing and hair lightening and curl reduction/straightening and improved frizz reduction for longer periods of time.

Furthermore, by employing the process of the present invention, straightening/relaxing or curl reduction of hair can be achieved in a manner which is less harmful to a user's skin and hair than conventional hair straightening/relaxing or curl reducing processes which employ large amounts of strong hydroxide compounds that can cause skin irritation, as well as damage to the hair itself.

Moreover, the subject composition and process avoids the use of formalin/formol or formaldehyde derivatives or formaldehyde-generating compounds that are employed in some conventional hair straightening/relaxing products and which are known to breakdown to formaldehyde with high heat and generate dangerous fumes.

In addition, the present invention does not require the use of ammonia, and/or peroxide compounds that are traditionally used in permanent hair coloring systems, and yet, is able to achieve the desired lightening/dyeing effects while minimizing damage to the hair fibers. Conversely, when greater lift of color is desired, ammonia may be used in the compositions of the present disclosure. Furthermore, the process according to the present disclosure can result in adequate gray hair coverage.

The compositions and methods of the present disclosure also provide a means for treating hair in an efficient and less messy or cleaner manner. A major disadvantage associated with the use of conventional permanent hair dye formulations and systems is that they are very messy to apply because the color is developed before it is applied onto the hair; they also have a tendency to cause scalp staining. Thus, it was found that the present disclosure provides a process for developing the color of the dye in situ, i.e., on the hair.

Moreover, the compositions of the present disclosure are easy and convenient to apply, do not run but remain localized at the point of application, and have improved dyeing properties. The term "improved dyeing properties" is understood to mean an improvement in the power/intensity, chromaticity and/or uniformity of the dyeing result.

It is to be understood that the foregoing describes various exemplary embodiments of the invention, but that modifications may be made therein without departing from the spirit or scope of the invention as set forth in the claims.

Composition for Dyeing and Reducing Curl and/or Frizziness of Hair

Non-Hydroxide Base

Suitable non-hydroxide bases for use in the composition for dyeing and reducing curl and/or frizziness of hair of the present invention are those curl and/or frizziness of hair are bases having a pKa of from about 0 to about 15, preferably from about 1 to about 14, and more preferably from about 2 to about 13. These may be chosen from organic bases and inorganic bases.

Organic bases generally include nitrogen-containing bases which do not completely disassociate in water. Examples thereof include, but are not limited to, ethylamines, ethyleneamines, ethanolamines, quinoline, aniline, pyridine, basic amino acids, and their derivatives. Particularly preferred nitrogen-containing bases include ethylenediamines, monoethanolamines, triethanolamines, arginine, lysine, and their derivatives, and mixtures thereof. Most preferably, the non-hydroxide base is chosen from monoethanolamine (MEA) and triethanolamine.

Inorganic bases generally include alkali metal phosphates and carbonates such as, for example, sodium phosphate, potassium phosphate, sodium carbonate, sodium bicarbonate, potassium carbonate, potassium bicarbonate, and their derivatives.

Inorganic bases may also include alkali metals of carboxylates such as, for example, sodium acetate, potassium acetate, sodium citrate, and potassium citrate, and their derivatives.

Particularly preferred inorganic bases include potassium phosphate, sodium phosphate, and sodium carbonate.

The non-hydroxide base is typically employed in the composition for dyeing and reducing curl and/or frizziness of hair of the present disclosure in an amount of from about 0.1% to about 50% by weight, preferably from about 0.1% to about 30% by weight, preferably from about 0.1% to about 10% by weight, based on the total weight of the composition for dyeing and reducing curl and/or frizziness of hair.

Protein Denaturant

Suitable protein denaturants for use in the composition for dyeing and reducing curl and/or frizziness of hair of the present invention can be chosen from ureas, guanidines, amidines, urethanes, aromatic monohydroxylated, dihydroxylated, trihydroxylated or polyhydroxylated derivatives, nitrogen heterocycles of the imidazole or triazole family, carboxylic acids and amide and thioamide derivatives thereof, thioureas, amino acids, alcohols, polyols, amine oxides, surfactants containing sugar, choline, deoxycholine or polyethylene glycol units, metal salts and sulfamides.

As "urea" that may be used as relaxing active agent, this term refers to any derivative comprising in its chemical formula a carbonyl group simply bonded to 2 nitrogen atoms. These ureas are more particularly selected from the compounds of general formulae (I) and (II) below:

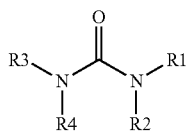

(I)

in which:
R1, R2, R3 and R4 represent, independently:
(i) a hydrogen atom, or
(ii) a linear or branched lower C1-C4 alkyl or alkenyl radical, optionally substituted with a radical chosen from: hydroxyl, amino, dimethylamino, carboxyl or carboxamide or N-methylcarboxamide.

When R1, R2 and R3 represent a hydrogen atom, R4 may also denote a radical chosen from the following: carboxamide; methoxy; ethoxy; 1,2,4-triazolyl; cyclopentyl; methoxycarbonyl; ethoxycarbonyl; CO——CH══CH——COOH; phenyl optionally substituted with a chlorine atom or a hydroxyl radical; benzyl; or 2,5-dioxo-4-imidazolidinyl.

When R1 and R3 represent a hydrogen atom, R2 may also represent a hydrogen atom or a methyl or ethyl radical and R4 an acetyl radical.

When R1=R2=H, R3 and R4 may also form, with the nitrogen atom that bears them, a piperidine or 3-methylpyrazole or 3,5-dimethylpyrazole or maleimide ring.

Finally, R1 and R2, and also R3 and R4, may also form, with the nitrogen atom that bears them, an imidazole ring.

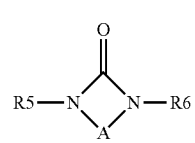

(II)

in which:
R5 and R6 represent, independently of each other:
(i) a hydrogen atom, or
(ii) a linear or branched C1-C4 lower alkyl radical, optionally substituted with a radical chosen from: hydroxyl, amino, dimethylamino, carboxyl or carboxamide.

and A represents the radicals: CH2——CH2 or CH══CH or CH2-CO or CO——NH or CH══N or CO——CO or CHOH——CHOH or (HOOC)CH——CH or CHOH——CO or CH2——CH2——CH2 or CH2-NH——CO or CH══C(CH3)——CO or NH——CO——NH or CH2——CH2——CO or CH2-N(CH3)——CH2 or NH——CH2——NH or CO——CH(CH3)——CH2 or CO——CH2——CO or CO——NH——CO or CO——CH(COOH)——CH2 or CO——CH══C(COOH) or CO——CH══C(CH3) or CO——C(NH2)══CH or CO——C(CH3)══N or CO——CH══CH or CO——CH══N or CO——N══CH.

As "guanidine" that may be used as relaxing active agent, this term means any derivative comprising in its chemical formula at least one carbon atom doubly bonded to a nitrogen atom and singly bonded to two other nitrogen atoms. These guanidines are more particularly selected from the compounds of general formula (III) below:

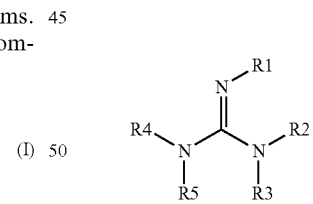

(III)

in which:
R1, R2, R3, R4 and R5 represent, independently:
(iii) a hydrogen atom, or
(iv) a linear or branched C1-C4 lower alkyl or alkenyl radical, optionally substituted with one or two radicals chosen from: hydroxyl, amino, dimethylamino, methoxy, ethoxy, carboxyl, carboxamide, N-methylcarboxamide or SO3H When R1, R2, R3 and R4 represent a hydrogen atom, R5 may also denote a radical chosen from the following: acetyl; chloroacetyl; carboxamide; methoxy; ethoxy; 1,2,4-triazolyl; cyclopentyl; methoxycarbonyl; ethoxycarbonyl; CO——CH══CH——COOH; phenyl optionally substituted with a chlorine atom or a hydroxyl radical; benzyl; thiazolidone; benzimidazole; benzoxazole; benzothiazole; or C(═NH)—NR6R7 in which R6 and R7 denote, independently of each other, a hydrogen atom or a linear or branched C1-C4 lower alkyl radical, optionally substituted with one or two radicals chosen from: hydroxyl, amino, dimethylamino, carboxyl and carboxamide; or N-methylcarboxamide; or alternatively a phenyl radical.

When R1=R2=R3=H, R4 and R5 may also form, with the nitrogen atom that bears them, a pyrrolidine, piperidine, pyrazole or 1,2,4-triazole ring, optionally substituted with one or two radicals chosen from: hydroxyl, amino and carboxyl.

When R1=R2=H, and R4=H or methyl, R3 and R5 may also together form a 5-membered ring optionally containing an oxo group, and the organic or mineral salts thereof.

In particularly preferred embodiments of the present disclosure, the at least one protein denaturant is chosen from urea, hydroxyethyl urea, and their derivatives.

In other particular embodiments of the present disclosure, the composition for dyeing and reducing curl and/or frizziness of hair comprises at least two protein denaturants. The at least two protein denaturants are preferably chosen from a urea or a guanidine, urea derivatives and/or salts, guanidine derivatives and/or salts, arginine, other compounds and their salts containing a guanidine moiety, and mixtures thereof. Preferably, the at least two protein denaturants may be chosen from urea and hydroxyethyl urea.

Preferably, the at least two protein denaturants are used in combination, present in a ratio by weight ranging from about 10:1 to about 1:10, or such as from about 8:1 to about 1:8, or such as from about 5:1 to about 2:1. In certain embodiments, the at least two protein denaturants are used in combination, present in a ratio by weight of such as from about 5:1, or such as from about 3:1, or such as from about 1:1, or preferably, from about 2:1.

Preferably, at least one of the protein denaturants is an organic amine having a pKb greater than 12; and more preferably, having a pKb greater than 13 at 25° C., such as for example, urea.

Some of the protein denaturants may also fit the description of the non-hydroxide base and therefore, can be used as the non-hydroxide base according to the invention. In such a case, the protein denaturant(s) in the composition for dyeing and reducing curl and/or frizziness of hair are different from the non-hydroxide base.

The protein denaturant is typically employed in the composition for dyeing and reducing curl and/or frizziness of hair of the present disclosure in an amount of from about 0.1% to about 50% by weight, preferably from about 0.5% to about 30% by weight, preferably from about 1% to about 25% by weight, even preferably from about 2% to about 20% by weight, based on the total weight of the composition for dyeing and reducing curl and/or frizziness of hair.

Dyes

The process of the present disclosure includes permanent or oxidation dyeing wherein the composition for dyeing and reducing curl and/or frizziness of hair comprises oxidative dye precursors. Typically the oxidative dye precursors ere selected from ortho- or para-phenylenediamines, ortho- or para-aminophenols and heterocyclic compounds. These oxidation bases are colourless or lightly coloured compounds which, in combination with oxidizing products, allow coloured species to be obtained, by a process of oxidative condensation.

Useful oxidative dye precursors of the present disclosure include, by way of example only, aromatic diamines, polyhydric phenols, amino phenols, and derivatives of these compounds, such as, for example, N-substituted derivatives of the amines, and ethers of the phenols.

By way of non-limiting example, oxidative dye precursors may be chosen from ortho- or para-aminophenols, ortho- or para-phenylenediamines, double bases, heterocyclic bases, and the acid addition salts thereof.

Exemplary para-phenylenediamines which may be chosen include compounds of the general formula (IV) and their addition salts with an acid:

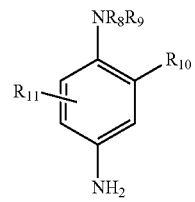

wherein, in formula (IV):
R8 represents a hydrogen atom, a C1-C4 alkyl radical, a C1-C4 monohydroxyalkyl radical, a C2-C4 polyhydroxyalkyl radical, a (C1-C4)alkoxy(C1-C4)alkyl radical, a C1-C4 alkyl radical substituted by a nitrogenous group, a phenyl radical or a 4'-aminophenyl radical;
R9 represents a hydrogen atom, a C1-C4 alkyl radical, a C1-C4 monohydroxyalkyl radical, a C2-C4 polyhydroxyalkyl radical, a (C1-C4)alkoxy(C1-C4)alkyl radical or a C1-C4 radical substituted by a nitrogenous group;
R8 and R9 can also form, with the nitrogen atom which carries them, a 5- or 6-membered nitrogenous heterocycle optionally substituted by one or more alkyl, hydroxyl or ureido groups;
R10 represents a hydrogen atom, a halogen atom, such as a chlorine atom, a C1-C4 alkyl radical, a sulpho radical, a carboxyl radical, a C1-C4 monohydroxyalkyl radical, a C1-C4 hydroxyalkoxy radical, a C1-C4 acetylaminoalkoxy radical, a C1-C4 mesylaminoalkoxy radical or C1-C4 carbamoylaminoalkoxy radicals; and
R11 represents a hydrogen atom, a halogen atom or a C1-C4 alkyl radical.

By way of example, among the nitrogenous groups in the above formula (IV), of the amino, mono(C1-C4)alkylamino, di(C1-C4)alkylamino, tri(C1-C4)alkylamino, monohydroxy (C1-C4)alkylamino, imidazolinium and ammonium radicals may be chosen. Exemplary para-phenylenediamines of above formula (XXIII), include para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(beta-hydroxyethyl)-para-phenylenediamine, 4-N,N-bis(beta-hydroxyethyl)amino-2-methylaniline, 4-N,N-bis(beta-hydroxyethyl)amino-2-chloroaniline, 2-(beta-hydroxyethyl)-para-phenylenediamine, 2-fluoro-para-phenylenediamine, 2-isopropyl-para-phenylenediamine, N-(beta-hydroxypropyl)-para-phenylenediamine, 2-hydroxymethyl-para-phenylenediamine, N,N-dimethyl-beta-methyl-para-phenylenediamine, N-ethyl-N-(beta-hydroxyethyl)-para-phenylenediamine, N-(beta,gamma-dihydroxypropyl)-para-phenylenediamine, N-(4'-aminophenyl)-para-phenylenediamine, N-phenyl-para-phenylenediamine, 2-((beta-hydroxyethyloxy)-para-phenylenediamine, 2-((beta-acetylaminoethyloxy)-para-phenylenediamine, N-(beta-methoxyethyl)-para-phenylenediamine, 2-methyl-1-N-(beta-hydroxyethyl)-para-phenylenediamine and their addition salts with an acid.

Exemplary ortho-phenylenediamines, include N1-(2-hydroxyethyl)-4-nitro-o-phenylenediamine, 4-methyl-o-phenylenediamine, and 4-nitro-o-phenylenediamine and acid addition salts thereof.

As used herein, the term "double bases" means compounds comprising at least two aromatic nuclei having at least one of amino and hydroxyl groups. For example, double bases may be chosen from compounds of the formula (V) and their addition salts with an acid:

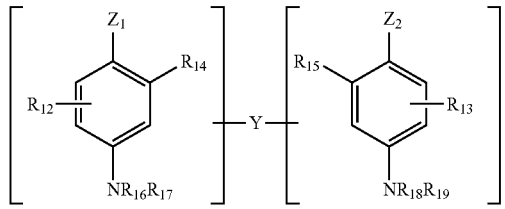

wherein, in formula (V):

Z1 and Z2 may independently be chosen from a hydroxyl or ——NH2 radical which can be substituted by a C1-C4 alkyl radical or by a connecting arm Y;

the connecting arm Y is chosen from a linear or branched alkylene chain comprising from 1 to 14 carbon atoms which can be interrupted or terminated by one or more nitrogenous groups and/or by one or more heteroatoms, such as oxygen, sulphur or nitrogen atoms, and which is optionally substituted by one or more hydroxyl or C1-C6 alkoxy radicals;

R12 and R13 are independently chosen from a hydrogen or halogen atom, a C1-C4 alkyl radical, a C1-C4 monohydroxyalkyl radical, a C2-C4 polyhydroxyalkyl radical, a C1-C4 aminoalkyl radical or a connecting arm Y;

R14, R15, R16, R17, R18 and R19 are independently chosen from a hydrogen atom, a connecting arm Y or a C1-C4 alkyl radical;

wherein compounds of formula (V) only comprise a single connecting arm Y per molecule.

In various embodiments, nitrogenous groups of the above formula (V), may be chosen from amino, mono(C1-C4)alkylamino, di(C1-C4)alkylamino, tri(C1-C4)alkylamino, monohydroxy(C1-C4)alkylamino, imidazolinium and ammonium radicals.

Nonlimiting examples of double bases include N,N'-bis(beta-hydroxyethyl)-N,N'-bis(4'-aminophenyl)-1,3-diamino-propan-ol, N,N'-bis(beta-hydroxyethyl)-N,N'-bis(4'-aminophenyl)ethylenediamine, N,N'-bis(beta-aminophenyl)-tetramethylenediamine, N,N'-bis(4-hydroxyethyl)-N,N'-bis(4-aminophenyl) tetramethylenediamine, N,N'-bis(4-methylaminophenyl) tetramethylenediamine, N,N'-diethyl-N,N'-bis(4'-amino-3'-methylphenyl)ethylenediamine, 1,8-bis(2,5-diaminophenoxy)-3,5-dioxaoctane, and their addition salts with an acid.

Non-limiting examples of para-aminophenols which can be used in the context of the invention can be chosen in particular from the compounds corresponding to the following formula (VI): and their addition salts with an acid:

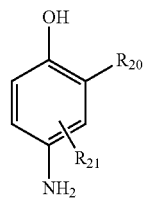

wherein, in formula (VI):

R20 is chosen from a hydrogen atom, a halogen atom, such as fluorine, a C1-C4 alkyl radical, a C1-C4 monohydroxyalkyl radical, a (C1-C4)alkoxy(C1-C4)alkyl radical, a C1-C4 aminoalkyl radical or a hydroxy(C1-C4) alkylamino-(C1-C4)alkyl radical, and R21 is chosen from a hydrogen atom, a halogen atom, such as fluorine, a C1-C4 alkyl radical, a C1-C4 monohydroxyalkyl radical, a C2-C4 polyhydroxyalkyl radical, a C1-C4 aminoalkyl radical, a C1-C4 cyanoalkyl radical or a (C1-C4)alkoxy(C1-C4)alkyl radical.

By way of example only, para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(beta-hydroxyethylaminomethyl)phenol, N-methyl-para-aminophenol, and the acid addition salts thereof may be chosen.

Exemplary ortho-aminophenols may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

Exemplary heterocyclic bases may be chosen from pyridine derivatives, pyrimidine derivatives, pyrazole derivatives, pyrazolinone derivatives, and the acid addition salts thereof.

Non-limiting examples of pyridine derivatives include, for example, those disclosed in GB1026978 and GB1153196, both incorporated by reference herein, such as 2,5-diaminopyridine, 2-(4-methoxyphenyl)amino-3-aminopyridine, 2,3-diamino-6-methoxypyridine, 2-(beta-methoxyethyl) amino-3-amino-6 methoxypyridine, 3,4-diaminopyridine, and the acid addition salts thereof.

Non-limiting examples of pyrimidine derivatives include, for example, those described in DE 2 359 399, JP 88-169 571, JP 91-10659 and WO 96/15765, all incorporated by reference herein, such as 2,4,5,6-tetra-aminopyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-triaminopyrimidine, and the pyrazolopyrimidine derivatives, such as those mentioned in French Application FR-A-2 750 048 and among which may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethyl-pyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-(imidazolylpropylamino)pyrazolo[1,5- a]pyrimidine; and their addition salts and their tautomeric forms, when there exists a tautomeric equilibrium, and their addition salts with an acid.

Non-limiting examples of pyrazole and pyrazolinone derivatives include the compounds described in DE 3,843, 892, DE 4,133,957, WO 94/08969, WO 94/08970, FR-A-2, 733,749, and DE 195 43 988, all of which are incorporated by reference herein, such as 4,5-diamino-1-methyl-pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(beta-hydroxyethyl)-3-methylpyrazole, 4,5-diamino-1-(beta-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(p-hydroxyethyl) amino-1-methylpyrazole, 2-(4,5-diamino-1H-pyrazol-1-yl), H2SO4, 2,3-diamino-6,7-dihydro-1H,5H-pyrazolo[1,2-z] pyrazol-1-one, 1-methyl-3-phenyl-2-pyrazolinone, and the acid addition salts thereof.

The at least one oxidation dye precursor may be present in the composition for dyeing and reducing curl and/or frizziness of hair of the present disclosure in an amount ranging from, for example, about 0.0001% to about 12%, such as from about 0.0001% to about 8.0%, or from about 0.005% to about 5% by weight, based on the total weight of the composition for dyeing and reducing curl and/or frizziness of hair.

This mode of coloring makes use, more particularly, of one or more oxidative dye precursors, even more particularly, of one or more oxidative dye precursors in combination with one or more couplers.

The shades obtained with the use of oxidative dye precursors are very often varied by combining them with one or more couplers, the latter being selected in particular from aromatic meta-diamines, meta-aminophenols, meta-diphenols and certain heterocyclic compounds, such as indole compounds.

The variety of the molecules employed for the oxidation bases and couplers allows a rich palette of colours to be obtained.

Direct dyes may be used in combination with oxidative dyes to produce a lightening effect. The direct dyes are colored molecules and are generally chosen from nitro (hetero) aryl direct dyes, especially nitrobenzene and nitropyridine, anthraxquinone, nitropyridine, azo, methine, azomethine, xanthene, acridine, azine, carbonyl and tri (hetero) arylmethane direct dyes, and the addition salts thereof; alone or as mixtures. The presence of such compounds enables the obtained coloration to be further enriched with tints or enables the chromaticity of the obtained coloration to be increased.

More particularly, the azo dyes comprise an —N=N-function in which the two nitrogen atoms are not simultaneously engaged in a ring. However, it is not excluded for one of the two nitrogen atoms of the sequence —N=N— to be engaged in a ring.

The dyes of the methine family are, for example, compounds comprising at least one sequence chosen from >C=C< and —N=C< in which the two atoms are not simultaneously engaged in a ring. However, it is pointed out that one of the nitrogen or carbon atoms of the sequences may be engaged in a ring. More particularly, the dyes of this family are derived from compounds of true methine type (comprising one or more abovementioned sequences —C=C—); of azomethine type (comprising at least one, or more, sequences —C=N—) with, for example, azacarbocyanins and their isomers, diazacarbocyanins and their isomers, and tetraazacarbocyanins; of mono- and diarylmethane type; of indoamine (or diphenylamine) type; of indophenol type; or of indoaniline type.

As regards the dyes of the carbonyl family, examples that may be mentioned include dyes chosen from acridone, benzoquinone, anthraquinone, naphthoquinone, benzanthrone, anthranthrone, pyranthrone, pyrazol-anthrone, pyrimidinoanthrone, flavanthrone, idanthrone, flavone, (iso) violanthrone, isoindolinone, benzimid-azolone, isoquinolinone, anthrapyridone, pyrazolo-quinazolone, perinone, quinacridone, quinophthalone, indigoid, thioindigo, naphthalimide, anthrapyrimidine, diketopyrrolopyrrole and coumarin dyes.

As regards the dyes of the azine family, mention may be made, for example, of azine, xanthene, thioxanthene, fluorindine, acridine, (di)oxazine, (di)thiazine and pyronin dyes.

As regards the dyes of porphyrin or phthalocyanin type, it is possible to use cationic or non-cationic compounds, optionally comprising one or more metals or metal ions, for instance alkali metals, alkaline-earth metals, zinc and silicon.

Other suitable synthetic direct dyes include monochromophoric cationic direct dyes of the following types: azos; methines; azomethines with diazacarbocyanins and isomers thereof, and tetraazacarbocyanins; anthraquinones; naphthoquinone or benzoquinone dyes; indoamine direct dyes; indigoid direct dyes; phthalocyanin and porphyrin direct dyes; alone or as mixtures.

As other dyes that may be used according to the invention, mention may also be made, among the azo direct dyes, of the following dyes: Disperse Red 17; Disperse Red 13; Basic Red 22; Basic Red 76; Basic Yellow 57; Basic Brown 16; Basic Brown 17; Disperse Green 9; Disperse Black 9; Solvent Black 3; Disperse Blue 148; Disperse Violet 63; and Solvent Orange 7.

Mention may also be made of 1-(4'-aminodiphenylazo)-2-methyl-4-bis(beta-hydroxyethyl)amino-benzene (INCI name: HC Yellow 7).

Among the quinone direct dyes that may be mentioned are the following dyes: Disperse Red 15; Solvent Violet 13; Solvent Blue 14; Disperse Violet 1; Disperse Violet 4; Disperse Blue 1; Disperse Violet 8; Disperse Blue 3; Disperse Red 11; Disperse Blue 7; Disperse Blue 14; Basic Blue 22; Disperse Violet 15; Disperse Blue 377; Disperse Blue 60; Basic Blue 99; and also the following compounds: 1-N-methylmorpholiniumpropylamino-4-hydroxyanthra-quinone; 1-aminopropylamino-4-methylaminoanthraquinone; 1-aminopropylamino-anthraquinone; 5-beta-hydroxyethyl-1,4-diaminoanthraquinone; 2-aminoethylaminoanthraquinone; and 1,4-bis(beta-dihydroxypropylamino) anthraquinone.

Mention may also be made of the coumarin compound Disperse Yellow 82.

Among the azine dyes that may be mentioned are the following compounds: Basic Blue 17; Basic Red 2; Solvent Orange 15.

Among the triarylmethane dyes that may be used according to the invention, mention may be made of the following compounds: Basic Green 1; Basic Violet 3; Basic Violet 14; Basic Blue 7; Basic Blue 26.

Among the indoamine dyes that may be used according to the invention, mention may be made of the following compounds: 2-hydroxyethylamino-5-[bis(beta-4'-hydroxyethyl) amino]anilino-1,4-benzoquinone; 2-hydroxyethylamino-5-(2'-methoxy-4'-amino)anilino-1,4-benzoquinone; 3-N(2'-chloro-4'-hydroxy)phenylacetylamino-6-methoxy-1,4-benzoquinone imine; 3-N(3'-chloro-4'-methylamino) phenylureido-6-methyl-1,4-benzoquinone imine; 3-[4'-N-(ethylcarbamylmethyl)amino]phenylureido-6-methyl-1,4-benzoquinone imine.

Exemplary direct dyes that may be used include those that are nonionic, anionic, and cationic.

The cationic direct dyes may be, for example, chosen from direct dyes of the following types: azos, methines; azomethines, with diazacarbocyanins and isomers thereof, and tetraazacarbocyanins (tetraazapentamethines); anthraquinones; alone or as a mixture.

Suitable cationic direct dyes, may be chosen from cationic mixed dyes including at least one chromophore, such as at least two chromophores. As used herein, "cationic mixed dye" means a dye whose cationic charge can form an integral part of the chromophore and/or of the linker, or alternatively a dye whose cationic charge is present via a substituent on the chromophore and/or on the linker. As used herein, "chromophore" means a radical derived from a dye, i.e. a radical of a molecule that has at least one absorption maximum in the visible region between 400 and 800 nm, this absorbance requiring no prior oxidation or any combination with other chemical species.

In various embodiments where the at least one dye is chosen from mixed cationic dyes, the at least one chromophore may be chosen from acridine, acridone, anthranthrone, anthrapyrimidine, anthraquinone, azine, azo, azomethine, benzanthrone, benzimidazole, benzimidazolone, benzindole, benzoxazole, benzopyran, benzothiazole, benzoquinone, bisazine, bis-isoindoline, carboxanilide, coumarin, cyanins, diazine, diketopyrrolopyrrole, dioxazine, diphenylamine, diphenylmethane and dithiazine chromophores, flavonoids, fluorindines, formazans, hydrazones, hydroxy ketones, indamines, indanthrones, indigoids, pseudo-indigoids, indophenols, indoanilines, isoindolines, isoindolines, isoindolinones, isoviolanthrones, lactones, methines, naphthalimides, naphthanilides, naphtholactams, naphthoquinones, nitro dyes, oxadiazoles, oxazines, perilones, perinones, perylenes, phenazines, phenothiazines, phthalocyanin, polyenes/carotenoids, porphyrins, pyranthrones, pyrazolanthrones, pyrazolones, pyrimidinoanthrones, pyronines, quinacridones, quinolines, quinophthalones, squaranes, stilbenes, tetrazoliums, thiazines, thioindigo, thiopyronines, triarylmethanes, and xanthenes.

For the nonionic dyes, compounds with a log P of greater than or equal to 2 may be chosen; log P value conventionally represents the partition coefficient of the dye between octanol and water.

Among the anionic direct dyes, mention may be made in particular of: Disperse Red 17; Acid Yellow 9; Acid Black 1; Acid Yellow 36; Acid Orange 7; Acid Red 33; Acid Red 35; Acid Yellow 23; Acid Orange 24; Acid Violet 43; Acid Blue 62; Acid Blue 9; Acid Violet 49; and Acid Blue 7.

In various embodiments, the at least one direct dye may be present in an amount ranging from about 0.001% to about 20% by weight, such as from about 0.005% to about 10% by weight, or from about 0.01% to about 5% by weight, based on the total weight of the composition.

It is also possible to add other non-oxidative colorants or dyes to the dyeing and curl/frizz reducing compositions of the present disclosure. Exemplary non-oxidative hair colorants include, but are not limited to, direct dyes, pigments, liposoluble dyes, nacreous pigments, pearling agents, leuco dyes, optical lightening colorants, natural colorants and optically-variable pigments, which are coloured, and colouring molecules that have affinity for fibers.

Non-limiting examples of natural dyes that may be chosen include lawsone, juglone, alizarin, purpurin, carminic acid, kermesic acid, laccaic acid, purpurogallin, anthragallol, protocatechaldehyde, indigo, isatin, curcumin, spinulosin, chlorophylls, chlorophyllines, orceins, haematin, haematoxylin, brazilin, brazileine, safflower dyes (for instance carthamine), flavonoids (with, for example, morin, apigenidin and sandalwood), anthocyans (of the apigeninidin type), carotenoids, tannins, sorghum and cochineal carmine, or mixtures thereof.

Extracts or decoctions containing these natural dyes, and especially henna-based extracts, may also be used.

For example, the natural dyes are chosen from lawsone, juglone, alizarin, purpurin, carminic acid, kermesic acid, laccaic acid, purpurogallin, protocatechaldehyde, indigo, isatin, curcumin, spinulosin, apigenidin, chlorophylline, sorghum, orceins, cochineal carmine, haematin, haematoxylin, brazilin and brazileine, and mixtures thereof.

These dyes may optionally be used in the presence of mordants (for example zinc, manganese, aluminium, iron, etc. salts).

Thickening Agent

The thickening agents of the present disclosure may also function as rheology-modifying agents.

The at least one thickening agent may be chosen from:

silicas, notably hydrophobic, such as those described in document EP-A-898960, and for example marketed under the references "AEROSIL R812" by the company Degussa, "CAB-O-SIL TS-530", "CAB-O-SIL TS-610", "CAB-O-SIL TS-720" by the company Cabot, "AEROSIL R972", "AEROSIL R974" by the company Degussa;

clays, such as montmorillonite, modified clays such as the bentones for example, stearalkonium hectorite, stearalkonium bentonite;

polysaccharide alkyl ethers (notably with the alkyl group having from 1 to 24 carbon atoms, preferably 1 to 10, more preferably 1 to 6, and more especially 1 to 3) such as those described in document EP-A-898958.

The at least one thickening agent may be chosen from nonionic amphiphilic polymers containing a hydrophobic chain, mention may be made, inter alia, of:

(1) celluloses modified with groups comprising at least one saturated or unsaturated, linear or branched C6-C30 hydrocarbon-based chain, for instance hydroxyethylcelluloses modified with groups comprising at least one hydrophobic chain as defined previously, such as especially Natrosol Plus Grade 330 CS (C16 alkyls——sold by the company Aqualon); Bermocoll EHM 100 (sold by the company Berol Nobel), Amercell Polymer HM-1500 (hydroxyethylcellulose modified with a polyethylene glycol (15) nonylphenyl ether group-sold by the company Amerchol);

(2) hydroxypropyl guars modified with groups comprising at least one hydrophobic chain as defined, for example Jaguar XC-95/3 (C14 alkyl chain-sold by the company Rhodia Chimie); Esaflor HM 22 (C22 alkyl chain-sold by the company Lamberti); RE210-18 (C14 alkyl chain) and RE205-1 (C20 alkyl chain-sold by the company Rhodia Chimie);

(3) copolymers of vinylpyrrolidone and of hydrophobic monomers containing a hydrophobic chain as defined above, for instance Antaron or Ganex V216 (vinylpyrrolidone/hexadecene copolymers); Antaron or Ganex V220 (vinylpyrrolidone/eicosene copolymers), sold by the company I.S.P.;

(4) copolymers of C1-C6 alkyl (meth)acrylates and of amphiphilic monomers containing a hydrophobic chain;

(5) copolymers of hydrophilic (meth)acrylates and of hydrophobic monomers comprising at least one hydrophobic chain, for instance the polyethylene glycol methacrylate/lauryl methacrylate copolymer;

(6) polymers with an aminoplast ether skeleton containing at least one fatty chain, such as the Pure Thix compounds sold by the company Sud-Chemie;

(7) linear (block structure), grafted, or starburst polyurethane polyethers comprising in their chain at least one hydrophilic block, which is generally a polyoxyethylene block which may comprise between 50 and 1000 oxyethylene units approximately, and at least one hydrophobic block, which may comprise aliphatic groups alone, optionally combined with cycloaliphatic and/or aromatic blocks. In various embodiments, the polyurethane polyethers comprise at least two C6-C30 hydrocarbon-based hydrophobic chains, separated by a hydrophilic block; the hydrophobic chains may be pendent chains or chains with one or more of the end groups of the hydrophilic block(s).

The polyurethane polyethers may comprise a urethane bond between the hydrophilic blocks, but may also contain hydrophilic blocks linked to the lipophilic blocks via other chemical bonds. Examples of polyurethane polyethers that may be used include, but are not limited to, Nuvis FX 1100 (European and US INCI name "Steareth-100/PEG-136/HMDI Copolymer" sold by the company Elementis Specialties); Rheolate® 205, 208, 204 or 212 (sold by the company Rheox) and also Acrysol RM 184® (sold by the company Rohm & Haas); Elfacos T210® (C12-C14 alkyl chain) and Elfacos T212® (C18 alkyl chain) sold by the company Akzo. The product DW 1206B® from Rohm and Haas comprising a C20 alkyl chain and comprising a urethane bond, provided at a solids content of 20 percent in water, can also be used.

Use may also be made of solutions or dispersions of these polymers, for example in water or in an aqueous/alcoholic medium, such as polymers of Rheolate® 255, Rheolate® 278 and Rheolate® 244, sold by Rheox, and DW 1206F and DW 1206J provided by Rohm and Haas.

In some embodiments, the at least one thickening agent are chosen from polymers of natural origin may include, for example, thickening polymers comprising at least one sugar unit, for instance nonionic guar gums, optionally modified with C1-C6 hydroxyalkyl groups; biopolysaccharide gums of microbial origin, such as scleroglucan gum or xanthan gum; gums derived from plant exudates, such as gum arabic, ghatti gum, karaya gum, gum tragacanth, carrageenan gum, agar gum and carob gum; pectins; alginates; starches; hydroxy(C1-C6)alkylcelluloses and carboxy(C1-C6)alkylcelluloses.

It should be noted that the term "sugar unit" denotes a monosaccharide (i.e. monosaccharide or oside or simple sugar) portion, an oligosaccharide portion (short chains formed from a sequence of monosaccharide units, which may be different) or a polysaccharide portion [long chains consisting of monosaccharide units, which may be different, i.e. polyholosides or polyosides]. The saccharide units may also be substituted with alkyl, hydroxyalkyl, alkoxy, acyloxy or carboxyl radicals, the alkyl radicals containing from 1 to 4 carbon atoms.

Non-limiting examples of nonionic, unmodified guar gums that may be used in various embodiments include Guargel D/15 (Noveon); Vidogum GH 175 (Unipectine), Meypro-Guar 50 and Jaguar C (Meyhall/Rhodia Chimie). Non-limiting examples of modified nonionic guar gums include Jaguar HP8, HP60, HP120, DC 293 and HP 105 (Meyhall/Rhodia Chimie); Galactasol 4H4FD2 (Aqualon).

Among these gums, mention will be made of scleroglucans such as, for example, Actigum CS from Sanofi Bio Industries; Amigel from Alban Muller International, and also the glyoxal-treated scleroglucans described in FR2633940); xanthan gums, for instance Keltrol®, Keltrol® T, Keltrol® Tf, Keltrol® Bt, Keltrol® Rd, Keltrol® Cg (Nutrasweet Kelco), Rhodicare® S and Rhodicare® H (Rhodia Chimie); starch derivatives, for instance Primogel® (Avebe); hydroxyethylcelluloses such as Cellosize® QP3L, QP4400H, QP30000H, HEC30000A and Polymer PCG10 (Amerchol), Natrosol 250HHR®, 250MR, 250M, 250HHXR, 250HHX, 250HR, HX (Hercules) and Tylose® H1000 (Hoechst); hydroxypropylcelluloses, for instance Klucel® EF, H, LHF, MF and G (Aqualon); carboxymethylcelluloses, for instance Blanose® 7M8/SF, refined 7M, 7LF, 7MF, 9M31F, 12M31XP, 12M31P, 9M31XF, 7H, 7M31, 7H3SXF (Aqualon), Aquasorb® A500 (Hercules), Ambergum® 1221 (Hercules), Cellogen® HP810A, HP6HS9 (Montello) and Primellose® (Avebe).

In other preferred embodiments, the at least one thickening agent are chosen from nonionic polymers which include, but are not limited to, nonionic cellulose derivatives such as hydroxyethylcelluloses modified by groups comprising at least one hydrophobic chain, such as alkyl, arylalkyl or alkylaryl groups, or their blends, and in which the alkyl groups are, for example, C8-C22 alkyl groups, such as the product Natrosol Plus Grade 330 CS® (C16 alkyls) sold by Aqualon or the product Bermocoll EHM 100® sold by Berol Nobel.

Cellulose derivatives modified by alkylphenyl polyalkylene glycol ether groups may also be chosen, such as the product Amercell Polymer HM-1500® sold by Amerchol.

In certain exemplary embodiments, the at least one thickening agent is chosen from cellulose derivatives, polysaccharides, gums, clays, fumed silica, acrylates, polyacrylamides, crosslinked polyacrylic acids, crosslinked acrylamide polymers and copolymers, crosslinked methacryloyloxyethltrimethyl-ammonium chloride homopolymers, and associative polymers. Said rheology-modifying agents may include, in particular embodiments, xanthan gum, gum arabic, ghatti gum, karaya gum, gum tragacanth, carrageenan gum, agar gum, carob gum, pectins, alginates, starches, hydroxy($C_1$-$C_6$) alkylcelluloses, carboxy($C_1$-$C_6$)alkylcelluloses, and mixtures thereof.

In preferred embodiments, the at least one thickening agent is nonionic or is an uncharged compound. Without intending to be bound by theory, it is believed that a thickening agent comprising a charged compound could adversely interact with the dyes compounds, thereby affecting the solubility and stability of the dye compounds in the compositions of the present disclosure.

In particularly preferred embodiments, the at least one thickening agent is chosen from xanthan gum and guar gum.

The at least one thickening agent of the present disclosure may be employed in the composition for dyeing and reducing curl and/or frizziness of hair of the of the present disclosure in an amount ranging from, for example, about 0.05 to about 20% by weight, preferably from about 0.5 to about 15% by weight and more preferably from about 1 to about 10% by weight, based on the total weight of the composition for dyeing and reducing curl and/or frizziness of hair.

Fatty Substance

Exemplary fatty substances that may be used in various embodiments of the disclosure include, but are not limited to, organic compounds that are insoluble in water at normal temperature (25° C.) and at atmospheric pressure (760 mmHg) (solubility below 5% and such as below 1% and further such as below 0.1%). Fatty substances have in their structure a chain of at least two siloxane groups, or at least one hydrocarbon chain having at least 6 carbon atoms. Moreover, fatty substances are generally soluble in organic solvents in the same conditions of temperature and pressure, for example in chloroform, ethanol, benzene or decamethylcyclopentasiloxane.

Fatty substances may be, for example, chosen from lower alkanes, fatty alcohols, esters of fatty acid, esters of fatty alcohol, oils such as mineral, vegetable, animal and synthetic non-silicone oils, non-silicone waxes and silicones.

In some embodiments, the alcohols and esters have at least one linear or branched, saturated or unsaturated hydrocarbon group, comprising 6 to 30 carbon atoms, optionally substituted, for example, with at least one hydroxyl group (for example 1 to 4). If they are unsaturated, these compounds can have one to three, conjugated or unconjugated, carbon-carbon double bonds.

With regard to the lower alkanes, in some embodiments, these have from 6 to 16 carbon atoms and are linear or branched, optionally cyclic. As examples, alkanes can be chosen from hexane and dodecane, isoparaffins such as isohexadecane and isodecane.

Examples of non-silicone oils that may be used in various embodiments of the disclosure, include, but are not limited to, hydrocarbon oils of animal origin, such as perhydrosqualene; hydrocarbon oils of vegetable origin, such as liquid triglycerides of fatty acids having from 6 to 30 carbon atoms such as triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, shea butter oil; hydrocarbons with more than 16 carbon atoms, linear or branched, of mineral or synthetic origin, such as paraffin oils, petroleum jelly, liquid paraffin, polydecenes, hydrogenated polyisobutene such as Parleam®, fluorinated, partially hydrocarbon oils; as fluorinated oils, non-limiting examples include perfluoromethylcyclopentane and perfluoro-1,3-dimethylcyclohexane, sold under the names "FLUTEC® PC1" and "FLUTEC® PC3" by the company BNFL Fluorochemicals; perfluoro-1,2-dimethylcyclobutane; perfluoroalkanes such as dodecafluoropentane and tetradecafluorohexane, sold under the names "PF 5050" and "PF 5060®" by the 3M Company, or bromoperfluorooctyl sold under the name "FORALKYL®" by the company Atochem; nonafluoro-methoxybutane and nonafluoroethoxyisobutane; derivatives of perfluoromorpholine, such as 4-trifluoromethyl perfluoromorpholine sold under the name "PF 5052®" by the 3M Company.

The fatty alcohols that may be chosen as the at least one fatty substance include, but are not limited to, non-alkoxylated, saturated or unsaturated, linear or branched, and have from 6 to 30 carbon atoms and more particularly from 8 to 30 carbon atoms, such ascetyl alcohol, stearyl alcohol and their mixture (cetylstearyl alcohol), octyldodecanol, 2-butyloctanol, 2-hexyldecanol, 2-undecylpentadecanol, oleic alcohol or linoleic alcohol.

The exemplary non-silicone wax or waxes that can be used may be chosen from carnauba wax, candelilla wax, Alfa wax, paraffin wax, ozokerite, vegetable waxes such as olive wax, rice wax, hydrogenated jojoba wax, or absolute waxes of flowers, such as the essential wax of blackcurrant flower sold by the company BERTIN (France), animal waxes such as beeswaxes, or modified beeswaxes (cerabellina), or marine waxes such as that sold by the company SOPHIM under reference M82, or waxes of polyethylene, or of polyolefins in general.

Exemplary fatty acid esters are the esters of saturated or unsaturated, linear or branched C1-C26 aliphatic mono- or polyacids and of saturated or unsaturated, linear or branched C1-C26 aliphatic mono- or polyalcohols, the total number of carbons of the esters being, for example, greater than or equal to 10.

Among the monoesters, non-limiting mentions can be made of dihydroabietyl behenate; octyldodecyl behenate; isocetyl behenate; cetyl lactate; C12-C15 alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl, stearyl myristate, hexyl stearate, butyl stearate, isobutyl stearate; dioctyl malate, hexyl laurate, and 2-hexyldecyl laurate.

Further non-limiting examples of esters include esters of C4-C22 di- or tricarboxylic acids and of C1-C22 alcohols and the esters of mono-, di- or tricarboxylic acids and of C2-C26 di-, tri-, tetra- or pentahydroxy alcohols.

Even further non-limiting examples of esters include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisotearyl citrate; glyceryl trilactate; glyceryl trioctanoate; trioctyldodecyl citrate; trioleyl citrate, propylene glycol dioctanoate; neopentyl glycol diheptanoate; diethylene glycol diisanonate; and polyethylene glycol distearates.

Among the esters mentioned above, exemplary esters include ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate and isononyl isononanate, cetyl octanoate.

The composition can also comprise, as fatty ester, esters and di-esters of sugars of C6-C30, such as C12-C22 fatty acids. "Sugar" as used here means oxygen-containing hydrocarbon compounds that possess several alcohol functions, with or without aldehyde or ketone functions, and having at least 4 carbon atoms. These sugars can be monosaccharides, oligosaccharides or polysaccharides.

As suitable sugars, non-limiting examples include sucrose, glucose, galactose, ribose, fucose, maltose, fructose, mannose, arabinose, xylose, lactose, and their derivatives, for example alkylated, such as methylated derivatives such as methylglucose.

The esters of sugars and of fatty acids may be, for example, chosen from the esters or mixtures of esters of sugars described previously and of linear or branched, saturated or unsaturated C6-C30, such as C12-C22 fatty acids. If they are unsaturated, these compounds can have one to three, conjugated or unconjugated, carbon-carbon double bonds.

The esters according to at least one embodiment can also be chosen from mono-, di-, tri- and tetra-esters, polyesters and mixtures thereof.

These esters can be, for example, oleate, laurate, palmitate, myristate, behenate, cocoate, stearate, linoleate, linolenate, caprate, arachidonates, or mixtures thereof such as the oleo-palmitate, oleo-stearate, palmito-stearate mixed esters.

For example, the mono- and di-esters can be used, and such as the mono- or di-oleate, stearate, behenate, oleopalmitate, linoleate, linolenate, oleostearate, of sucrose, of glucose or of methylglucose.

One non-limiting example useful in various embodiments includes the product sold under the name GLUCATE® DO by the company Amerchol, which is a dioleate of methylglucose.

Exemplary esters or mixtures of esters of sugar of fatty acid include: the products sold under the names F160, F140, F110, F90, F70, SL40 by the company Crodesta, denoting respectively the palmito-stearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and the monolaurate of sucrose; the products sold under the name Ryoto Sugar Esters for example with the reference B370 and corresponding to the behenate of sucrose formed from 20% of monoester and 80% of di-triester-polyester; sucrose mono-di-palmito-stearate marketed by the company Goldschmidt under the name TEGOSOFT® PSE.

Silicones usable in the composition of the present disclosure include but are not limited to volatile or non-volatile, cyclic, linear or branched silicones, modified or not with organic groups, having a viscosity from 5×10-6 to 2.5 m2/s at 25° C., such as from 1 x'10-5 to 1 m2/s.

The silicones usable according to the disclosure can be in the form of oils, waxes, resins or gums.

In some embodiments, the silicone may be chosen from the polydialkylsiloxanes, such as the polydimethylsiloxanes (PDMS), and the organo-modified polysiloxanes having at least one functional group chosen from the poly(alkoxylated) groups, the amine groups and the alkoxy groups.

The organopolysiloxanes are defined in more detail in the work of Walter NOLL "Chemistry and Technology of Silicones" (1968), Academic Press. They can be volatile or non-volatile.

When they are volatile, the silicones are, for example, chosen from those with a boiling point between 60° C. and 260° C. By way of example, the silicones may be chosen from cyclic polydialkylsiloxanes having from 3 to 7, such as from 4 to 5, silicon atoms. Various exemplary silicones may be the octamethylcyclotetrasiloxane marketed under the name VOLATILE SILICONE® 7207 by UNION CARBIDE or SILBIONE® 70045 V2 by RHODIA, the decamethylcyclopentasiloxane marketed under the name VOLATILE SILICONE® 7158 by UNION CARBIDE, and SILBIONE® 70045 V5 by RHODIA, and mixtures thereof.

Non-limiting examples may also include the cyclocopolymers of the dimethylsiloxanes/methylalkylsiloxane type, such as SILICONE VOLATILE® FZ 3109 marketed by the company UNION CARBIDE, of the following formula (VVI):

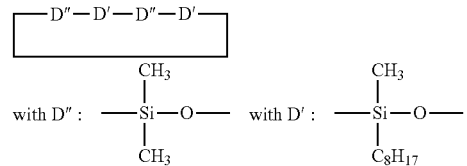

Further non-limiting examples may include mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy)bis-neopentane.

Other suitable volatile silicones include the linear volatile polydialkylsiloxanes having 2 to 9 silicon atoms and with a viscosity less than or equal to 5×10-6 m2/s at 25° C. One non-limiting example is decamethyltetrasiloxane, marketed under the name "SH 200" by the company TORAY SILICONE. Silicones included in this class are also described in the article published in Cosmetics and Toiletries, Vol. 91, Jan. 76, p. 27-32-TODD BYERS "Volatile Silicone fluids for cosmetics," which is incorporated by reference herein.

Even further non-limiting mentions can be made of non-volatile polydialkylsiloxanes, gums and resins of polydialkylsiloxanes, polyorganosiloxanes modified with the aforementioned organofunctional groups, and mixtures thereof.

These silicones may be, for example, chosen from the polydialkylsiloxanes, such as the polydimethylsiloxanes with trimethylsilyl end groups. The viscosity of the silicones is measured at 25° C. according to Standard Test Method for Kinematic Viscosity of Transparent and Opaque Liquids (and Calculation of Dynamic Viscosity).

Among these polydialkylsiloxanes, mention can be made of, non-exhaustively, the following commercial products: the SILBIONE® oils of series 47 and 70 047 or the MIRASIL® oils marketed by RHODIA, for example the oil 70 047 V 500,000; the oils of the MIRASIL® series marketed by the company RHODIA; the oils of the 200 series from the company DOW CORNING such as DC200, with a viscosity of 60,000 mm2/s; the VISCASIL® oils from GENERAL ELECTRIC and certain oils of the SF series (SF 96, SF 18) from GENERAL ELECTRIC.

Non-limiting mention can also be made of the polydimethylsiloxanes with dimethylsilanol end groups known under the name of dimethiconol (CTFA), such as the oils of the 48 series from the company RHODIA.

In this class of polydialkylsiloxanes, non-limiting mentions can be made of the products marketed under the names "ABIL WAX® 9800 and 9801" by the company GOLDSCHMIDT, which are polydialkyl (C1-C20) siloxanes.

The silicone gums usable according to the disclosure are, for example, polydialkylsiloxanes, such as polydimethylsiloxanes with high number-average molecular weights between 200,000 and 1,000,000 used alone or mixed in a solvent. This solvent can be chosen from the volatile silicones, the polydimethylsiloxane (PDMS) oils, the polyphenylmethylsiloxane (PPMS) oils, the isoparaffins, the polyisobutylenes, methylene chloride, pentane, dodecane, tridecane and mixtures thereof.

Products useful according to various embodiments of the disclosure include, for example, mixtures such as those formed from a chain end hydroxylated polydimethylsiloxane, or dimethiconol (CTFA) and a cyclic polydimethylsiloxane also called cyclomethicone (CTFA), such as the product Q2 1401 marketed by the company DOW CORNING; mixtures of a polydimethylsiloxane gum and a cyclic silicone such as the product SF 1214 Silicone Fluid from the company GENERAL ELECTRIC, said product being a gum SF 30 corresponding to a dimethicone, having a number-average molecular weight of 500,000, dissolved in the oil SF 1202 Silicone Fluid corresponding to decamethylcyclopentasiloxane; mixtures of two PDMS of different viscosities, for example, of a PDMS gum and a PDMS oil, such as the product SF 1236 from the company GENERAL ELECTRIC. The product SF 1236 is a mixture of a gum SE 30 as defined above having a viscosity of 20 m2/s and an oil SF 96 with a viscosity of 5×10-6 m2/s. This product, for example, has 15% of gum SE 30 and 85% of oil SF 96.

The organopolysiloxane resins usable according to the disclosure include, but are not limited to, crosslinked siloxane systems containing the units: R2SiO2/2, R3SiO1/2, RSiO3/2 and SiO4/2, wherein R represents an alkyl having from 1 to 16 carbon atoms. For example, R may denote a C1-C4 lower alkyl group, such as methyl.

Among these resins, non-limiting mention can be made of the product marketed under the name "DOW CORNING® 593" or those marketed under the names "SILICONE FLUID SS 4230 and SS 4267" by the company GENERAL ELECTRIC, which are silicones of dimethyl/trimethyl siloxane structure.

Non-limiting mention can also be made of the resins of the trimethylsiloxysilicate type, such as those marketed under the names X22-4914, X21-5034 and X21-5037 by the company SHIN-ETSU.

The organomodified silicones usable according to the disclosure include but are not limited to silicones as defined previously, having in their structure at least one organofunctional group fixed by a hydrocarbon group.

In addition to the silicones described above, the organomodified silicones can be polydiaryl siloxanes, such as polydiphenylsiloxanes, and polyalkyl-arylsiloxanes functionalized by the aforementioned organofunctional groups.

The polyalkarylsiloxanes are, for example, chosen from the polydimethyl/methylphenylsiloxanes, the polydimethyl/diphenylsiloxanes, linear and/or branched, with viscosity ranging from 1×10-5 to 5×102 m2/s at 25□.

Among these polyalkarylsiloxanes, non-limiting mention can be made of the products marketed under the following names: the SILBIONE® oils of series 70 641 from RHODIA; the oils of the series RHODORSIL® 70 633 and 763 from RHODIA; the oil DOW CORNING® 556 COSMETIC GRADE FLUID from DOW CORNING; the silicones of the PK series from BAYER such as the product PK20; the silicones of the series PN, PH from BAYER such as the products PN1000 and PH1000; certain oils of the SF series from GENERAL ELECTRIC such as SF 1023, SF 1154, SF 1250, SF 1265.

Among the organomodified silicones, non-limiting mention can be made of the polyorganosiloxanes having: polyoxyethylene and/or polyoxypropylene groups optionally with C6-C24 alkyl groups such as the products called dimethicone copolyol marketed by the company DOW CORNING under the name DC 1248 or the oils SILWET® L 722, L 7500, L 77, L 711 from the company UNION CARBIDE and the alkyl (C12)-methicone copolyol marketed by the company DOW CORNING under the name Q2 5200; substituted or unsubstituted amine groups such as the products marketed under the name GP 4 Silicone Fluid and GP 7100 by the company GENESEE or the products marketed under the names Q2 8220 and DOW CORNING® 929 or 939 by the company DOW CORNING. The substituted amine groups are, for example, C1-C4 aminoalkyl groups; alkoxylated groups, such as the product marketed under the name "SILICONE COPOLYMER F-755" by SWS SILICONES and ABIL WAX® 2428, 2434 and 2440 by the company GOLDSCHMIDT.

In various exemplary embodiments, the at least one fatty substance is neither alkoxylated, nor glycerolated. For example, the at least one fatty substance may be chosen from compounds that are liquid or pasty at room temperature and atmospheric pressure. By way of example, the at least one fatty substance may be a compound that is liquid at a temperature of 25° C., and atmospheric pressure.

Exemplary fatty substances may be, for example, chosen from the lower alkanes, fatty alcohols, esters of fatty acid, esters of fatty alcohol, and oils such as non-silicone mineral, vegetable and synthetic oils, the silicones.

According to at least one embodiment, the at least one fatty substance, is chosen from liquid paraffin, polydecenes, liquid esters of fatty acids and of fatty alcohols, non-silicone oils and mixtures thereof.

In some embodiments, the at least one fatty substance is chosen from alkanes, hydrocarbons and silicones.

In further exemplary embodiments, the at least one fatty substance may be chosen from fatty acids having from example, from about 6 to about 40 carbon atoms such as Arachidic Acid, Arachidonic Acid, Beeswax Acid, Capric Acid, Caproic Acid, Caprylic Acid, Coconut Acid, Isostearic Acid, Lauric Acid, Linoleic Acid, Linolenic Acid, Myristic Acid, Oleic Acid, Olive Acid, Palmitic Acid, Rapeseed Acid, Stearic Acid, Tallow Acid, Undecanoic Acid, Undecylenic Acid, Wheat Germ Acid.

In various exemplary embodiments, fatty acids having from about 6 to about 40 carbon atoms are chosen from Capric Acid, Caprylic Acid, Lauric Acid, Oleic Acid, Isostearic Acid, and Stearic Acid.

In various embodiments, the at least one fatty substance may be present in the composition for dyeing and reducing curl and/or frizziness of hair of the of the present disclosure in an amount of at least about 10% by weight, such as from about 10% to about 80% by weight, such as from about 15% to about 65% by weight, or from about 20% to about 55% by weight, based on the total weight of the composition for dyeing and reducing curl and/or frizziness of hair.

Alkoxysilane

The composition for dyeing and reducing curl and/or frizziness of hair described above may include at least one alkoxysilane comprising at least one solubilizing functional group.

Suitable alkoxysilanes comprising at least one solubilizing functional group for use in the present invention include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyl, and polyether groups.

The at least one alkoxysilane present in the composition comprises at least one solubilizing functional group, which may be identical or different, such as those previously defined.

The at least one alkoxysilane comprising at least one solubilizing functional group present in the composition of the present disclosure may comprise at least one silicon atom, for example, one silicon atom.

The at least one alkoxysilane comprising at least one solubilizing functional group present in the composition may, in at least one embodiment, comprise two or three alkoxy functions. In another embodiment, the alkoxy functional groups are chosen from methoxy and ethoxy functional groups.

According to a further embodiment, the at least one alkoxysilane comprising at least one solubilizing functional group present in the composition of the present disclosure is chosen from compounds of formula (I):

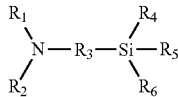
(I)

wherein:

$R_4$ is chosen from halogen atoms, OR' groups, and $R_{11}$ groups;

$R_5$ is chosen from halogen atoms, OR" groups, and $R_{12}$ groups;

$R_6$ is chosen from halogen atoms, OR'" groups, and $R_{13}$ groups;

$R_1$, $R_2$, $R_3$, R', R", R'", $R_{11}$, $R_{12}$, and $R_{13}$, which may be identical or different, are chosen from linear and branched, saturated and unsaturated hydrocarbon groups, optionally bearing at least one additional chemical group, wherein $R_1$, $R_2$, R', R", and R'" may also be chosen from hydrogen; at least two groups $R_4$, $R_5$, and $R_6$ are different from $R_{11}$, $R_{12}$, and $R_{13}$, and at least two groups R', R", and R'" are not hydrogen.

In at least one embodiment, the $R_1$, $R_2$, R', $R'_1$, $R'_2$, $R'_3$, R", and R'" groups are chosen from $C_1$-$C_{12}$ alkyl, $C_6$-$C_{14}$ aryl, $C_1$-$C_8$ alkyl-$C_6$-$C_{14}$ aryl, and $C_6$-$C_{14}$ aryl-$C_1$-$C_8$-alkyl radicals.

According to a second embodiment of the present disclosure, the at least one alkoxysilane comprising at least one solubilizing functional group present in the composition is chosen from compounds of formula (II):

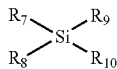
(II)

wherein:

$R_9$ is chosen from halogen atoms and $OR'_9$ groups and $R_{10}$ is chosen from halogen atoms and $OR'_{10}$ groups; wherein at least one of $R_9$ and $R_{10}$ is not a halogen;

$R'_9$ and $R'_{10}$, which may be identical or different, are chosen from hydrogen, and linear and branched, saturated and unsaturated $C_1$-$C_{14}$ hydrocarbon groups; wherein at least one of $R_9$ and $R_{10}$ is not hydrogen;

$R_7$ is a non hydrolyzable functional group providing a cosmetic effect, and $R_8$ is a non hydrolyzable functional group bearing at least one function chosen from: amines, carboxylic acids and salts thereof, sulfonic acids and salts thereof, polyols such as glycol, polyethers such as polyalkylene ether, and phosphoric acids and salts thereof.

As used herein, the term "functional group providing a cosmetic effect" means a group derived from an entity chosen from reducing agents, oxidizing agents, coloring agents, polymers, surfactants, antibacterial agents, and UV absorbing filters.

In at least one embodiment, the functional group providing a cosmetic effect is a group derived from a coloring agent.

According to a third embodiment of the present disclosure, the at least one alkoxysilane comprising at least one solubilizing functional group present in the composition of the present disclosure is chosen from compounds of formula (III):

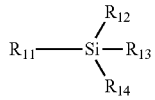
(III)

wherein:

$R_{12}$ is chosen from halogen atoms, $OR'_{12}$ groups, and $R_o$ groups;

$R_{13}$ is chosen from halogen atoms, $OR'_{13}$ groups, and $R'_o$ groups;

$R_{14}$ is chosen from halogen atoms, $OR'_{14}$ groups, and $R"_o$ groups;

wherein at least two groups $R_{12}$, $R_{13}$ and $R_{14}$ are different from $R_o$, $R'_o$, and $R"_o$ groups;

$R_{11}$ is a group chosen from groups bearing at least one function chosen from: carboxylic acids and salts thereof, sulfonic acids and salts thereof, and polyalkylethers; and Ro, R'o, R"o, $R'_{12}$, $R'_{13}$, and $R'_{14}$, which may be identical or different, are chosen from linear and branched, saturated and unsaturated, $C_1$-$C_{14}$ hydrocarbon groups optionally bearing at least one additional chemical functional group chosen from: carboxylic acids and salts thereof, sulfonic acids and salts thereof, and polyalkylether functions, wherein $R'_{12}$, $R'_{13}$, and $R_{14}$ may also be chosen from hydrogen, and wherein at least two of the groups $R'_{12}$, $R'_{13}$, and $R'_{14}$ are not hydrogen.

In at least one embodiment, the $R'_{12}$, $R'_{13}$, $R'_{14}$, $R_o$, $R'_o$, and $R"_o$ groups are chosen from $C_1$-$C_{12}$ alkyl groups, $C_6$-$C_{14}$ aryl groups, $C_1$-$C_8$ alkyl-$C_6$-$C_{14}$ aryl groups, and $C_6$-$C_{14}$ aryl-$C_1$-$C_8$ alkyl groups.

According to another embodiment of the present disclosure, the at least one alkoxysilane comprising at least one solubilizing functional group present in the composition of the present disclosure is chosen from compounds of formula (IV):

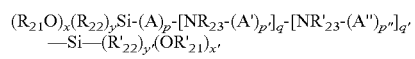
(IV)

wherein:

$R_{21}$, $R_{22}$, $R'_{21}$, and $R'_{22}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups, x is an integer ranging from 1 to 3, y=3−x, x' is an integer ranging from 1 to 3, y'=3−x', p=0 or 1, p'=0 or 1, p"=0 or 1, q=0 or 1, q'=0 or 1, wherein at least one of q or q' is not equal to zero, A, A', and A", which may be identical or different, are chosen from linear and branched $C_1$-$C_{20}$ alkylene divalent radicals, and $R_{23}$ and $R'_{23}$, which may be identical or different, are chosen from hydrogen and linear and branched, saturated and unsaturated hydrocarbon chains, optionally comprising at least one heteroatom, optionally interrupted by or substituted with at least one entity chosen from: ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_3$-$C_{20}$ alcohol ester, amine, amide, carboxyl, alkoxysilane, hydroxyl, carbonyl, and acyl groups.

As defined above, $R_{21}$, $R_{22}$, $R'_{21}$, and $R'_{22}$, which may be identical or different, may be chosen from hydrocarbon chains. As used herein, the term "hydrocarbon chain" means, for example, a chain comprising from 1 to 10 carbon atoms.

Likewise, $R_{23}$ and $R'_{23}$ may be chosen from hydrocarbon chains. In such an embodiment, the hydrocarbon chains may comprise from 1 to 10 carbon atoms.

According to one embodiment, the aromatic ring comprises from 6 to 30 carbon atoms. In another embodiment, the aromatic ring is an optionally substituted phenyl radical.

In at least one embodiment, in formula (IV) above:
$R_{21}$=$R'_{21}$,
$R_{22}$=$R'_{22}$,
x=x',
y=y',
p=p',
A=A',
q=1, and
q'=0.

According to a further embodiment, the at least one alkoxysilane comprising at least one solubilizing functional group used according to the present disclosure may also have at least one of the following characteristics:

$R_{21}$, $R_{22}$, $R'_{21}$, and $R'_{22}$, which may be identical or different, are chosen from $C_1$-$C_4$ alkyl groups;
p=p'=1;
A and A', which may be identical or different, are chosen from linear $C_1$-$C_4$ alkylene groups; and/or
$R_{23}$ is hydrogen.

According to this embodiment, the at least one alkoxysilane comprising at least one solubilizing functional group may be chosen from compounds of formula (V):

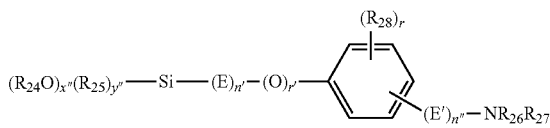

(V)

wherein:
$R_{24}$ and $R_{25}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups,
x"=2 or 3,
y"=3−x",
n"=0 or 1,
n'"=0 or 1,
E and E', which may be identical or different, are chosen from linear and branched $C_1$-$C_{20}$ alkylene divalent radicals,
$R_{26}$ and $R_{27}$, which may be identical or different, are chosen from hydrogen and linear and branched, saturated and unsaturated hydrocarbon chains, optionally comprising at least one heteroatom, optionally interrupted by or substituted with at least one entity chosen from: ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from: $C_1$-$C_{20}$ alcohol ester, amine, amide, carboxyl, alkoxysilane, hydroxyl, carbonyl, and acyl groups,
r is an integer ranging from 0 to 4,
r'=0 or 1, and
$R_{28}$, which may be identical or different, is chosen from hydrogen and linear and branched, saturated and unsaturated hydrocarbon chains, comprising, for example, from 1 to 10 carbon atoms and optionally at least one heteroatom, optionally interrupted by or substituted with at least one entity chosen from: ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from: $C_1$-$C_{20}$ alcohol ester, amine, amide, carboxyl, alkoxysilane, hydroxyl, carbonyl, and acyl groups.

As defined above, $R_{24}$ and $R_{25}$, which may be identical or different, may be chosen from hydrocarbon chains. As used herein, the term "hydrocarbon chain" is intended to mean a chain comprising, for example, from 1 to 10 carbon atoms.

Likewise, $R_{26}$ and $R_{27}$ may be chosen from hydrocarbon chains. In this embodiment, the hydrocarbon chains may comprise from 1 to 10 carbon atoms.

According to another embodiment, the aromatic ring comprises from 6 to 30 carbon atoms. In a further embodiment, the aromatic ring is an optionally substituted phenyl radical.

According to at least one embodiment, the at least one alkoxysilane comprising at least one solubilizing functional group used in accordance with the present disclosure may have at least one of the following characteristics:
$R_{24}$ is a $C_1$-$C_4$ alkyl group;
x"=3;
n'=n"=1;
r=r'=0; and/or
$R_{26}$ and $R_{27}$, which may be identical or different, are chosen from hydrogen and groups chosen from $C_1$-$C_4$ alkyl groups, $C_1$-$C_4$ hydroxyalkyl groups, and $C_1$-$C_4$ aminoalkyl groups.

According to a further embodiment of the present disclosure, the at least one alkoxysilane comprising at least one solubilizing functional group present in the composition is chosen from compounds of formula (VI):

$$(R_{29}O)x_1(R_{30})y_1\text{-Si-}(A_1)_s\text{-CH}=O \qquad (VI)$$

wherein:
$R_{29}$ and $R_{30}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups,
$x_1$=2 or 3,
$y_1$=3−$x_1$,
$A_1$ is chosen from linear and branched $C_1$-$C_{20}$ alkylene divalent radicals, optionally interrupted by or substituted with at least one group chosen from $C_1$-$C_{30}$ alcohol ester, amine, carboxyl, alkoxysilane, $C_6$-$C_{30}$ aryl, hydroxyl, and carbonyl groups, and
s=0 or 1.

As defined above, $R_{29}$ and $R_{30}$, which may be identical or different can be chosen from hydrocarbon chains. As used herein, the term "hydrocarbon chain" means a chain comprising, for example, from 1 to 10 carbon atoms.

In another embodiment, the at least one alkoxysilane comprising at least one solubilizing functional group may have at least one of the following characteristics:

$R_{29}$ and $R_{30}$, which may be identical or different, are chosen from $C_1$-$C_4$, alkyl groups;

s=1; and $A_1$ is a linear $C_1$-$C_4$ alkylene group.

According to this embodiment, the at least one alkoxysilane comprising at least one solubilizing functional group may be chosen from:

triethoxysilyl butyraldehyde, of formula:

(CH$_3$CH$_2$O)$_3$—S—(CH$_2$)$_3$—CH=O triethoxysilyl undecanal, of formula:

(CH$_3$CH$_2$O)$_3$—S—(CH$_2$)$_{10}$—CH=O and triethoxysilyl undecanal, ethylene glycol acetal, of formula:

(CH$_3$CH$_2$O)$_3$—Si—(CH$_2$)$_{10}$—CH(OCH$_2$)$_2$.

In a further embodiment, the at least one alkoxysilane comprising at least one solubilizing functional group is chosen from compounds of formula (VII):

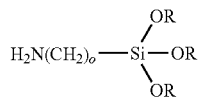
(VII)

wherein the R radicals, which may be identical or different, are chosen from $C_1$-$C_6$ alkyl radicals and n is an integer ranging from 1 to 6, for example, from 2 to 4.

In at least one embodiment, the at least one alkoxysilane comprising at least one solubilizing functional group present in the composition of the present disclosure is γ-aminopropyltriethoxysilane, also known as 3-aminopropyltriethoxysilane.

The alkoxysilanes useful in the present disclosure can be chosen from alkoxysilanes comprising a silicon atom of formula $R_{(4-n)}SiX_n$, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Possible examples of useful alkoxysilanes include 3-mercaptopropyltriethoxysilane and aminoalkyltrialkoxysilanes such as 3-aminopropyltriethoxysilane, as described in French Patent Application No. FR 2 789 896.

Other useful alkoxysilanes are cited, for example, in Patent Application EP 1 216 022, which describes alkoxysilanes comprising at least one hydrocarbon chain containing a non-basic solubilizing chemical function. In this respect, non-limiting mention may be made of the HCl-neutralized sodium N-[(3-trimethoxysilyl)propyl]ethylenediaminetriacetate supplied by GELEST.

According to at least one embodiment, the alkoxysilanes may comprise at least one hydrocarbon chain containing fluorine atoms. Possible examples include but are not limited to the 3,3,3-trifluoropropyltriethoxysilane or tridecafluorooctyltriethoxysilane compounds described in Patent Application EP 1 510 197.

In another embodiment, the useful alkoxysilanes may be alkoxysilanes which carry a group having a cosmetic functional group, such as aromatic nitro dyes or anthraquinone, napthoquinone, benzoquinone, azo, xanthene, triarylmethane, azine, indoaniline, indophenolic or indoamine dyes; groups having a reductive effect, such as thiol groups, sulphinic acid or sulphinic salt, it being possible for these alkoxysilanes to carry a solubilizing non-hydrolysable group such as amino groups, carboxylic acids, sulphonic acids, sulphates, quaternary ammoniums, polyalcohols, polyether and phosphates. One possible example includes aminopropyl-N-(4,2-dinitrophenyl)aminopropyldiethoxysilane. Compounds of this kind are described, for example, in Patent Application EP 1 216 023.

The alkoxysilanes of the present disclosure may be amino aryl alkoxysilanes. Possible examples include but are not limited to the following compounds:

3-(m-aminophenoxy)propyltrimethoxysilane, of the formula:

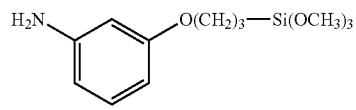

provided by GELEST, p-aminophenyltrimethoxysilane, of formula:

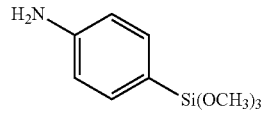

provided by GELEST, and

N-(2-aminoethylaminomethyl)phenethyltrimethoxysilane, of the formula:

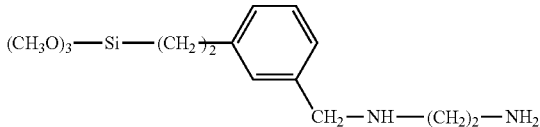

provided by GELEST.

According to at least one embodiment, the at least one organic silicon compound is N-(2-aminoethylaminomethyl) phenethyltrimethoxysilane.

The alkoxysilanes of the present disclosure may also be silanes having an aldehyde or acetal functional group, such as the triethoxysilylbutyraldehyde of formula (CH$_3$CH$_2$O)$_2$Si (CH$_2$)$_5$CHO or the triethoxysilylunedecanol ethylene glycol acetal (CH$_3$CH$_2$O)$_3$Si(CH$_2$)$_{10}$CH(OCH$_2$)$_2$, which are provided by GELEST.

The alkoxysilanes may also be silanes containing non-primary amines, such as the bis[3-(triethoxysilyl)propyl] amine of the formula (CH$_3$CH$_2$O)$_3$—Si(CH$_2$)$_3$NH(CH$_2$)$_3$Si (OCH$_2$CH$_3$)$_3$ provided by Fluorochem, the bis [trimethoxysilylpropyl]amine of the formula (CH$_3$O)$_3$—Si (CH$_2$)$_3$NH(CH$_2$)$_3$Si OCH$_3$)$_3$ provided by Gelest, the bis [methyldiethoxysilylpropyl]amine of the formula (CH$_3$CH$_2$O)$_2$CH$_3$Si (CH$_2$)$_3$NH(CH$_2$)$_3$SiCH$_3$(OCH$_2$CH$_3$)$_2$ provided by Gelest and the bis[3-trimethoxysilylpropyl]ethylenediamine of formula (CH$_3$O)$_3$Si(CH$_2$)$_3$NE(CH)$_2$NH (CH$_2$)$_3$Si(OCH$_3$)$_3$ provided by Gelest.

In another embodiment the at least one alkoxysilane is a trialkoxysilane comprising an amino substituent.

The at least one alkoxysilane comprising at least one solubilizing functional group may be present in the composition for dyeing and reducing curl and/or frizziness of hair from about 0.1% to about 10% by weight, preferably from about 0.25% to about 8% by weight, preferably from about 0.5% to about 5% by weight, based on the total weight of the composition for dyeing and reducing curl and/or frizziness of hair.

Cosmetically Acceptable Carrier

As used herein, the term "cosmetically acceptable carrier" is known to one of ordinary skill in the art, and may comprise, for example, water and/or at least one organic solvent.

Cosmetically acceptable carriers useful according to various embodiments described herein may, by way of non-limiting example, be chosen from water, organic solvents, natural oils, synthetic oils, esters, hydrocarbons, silicones, and mixtures thereof. Non-limiting examples of cosmetically acceptable carriers include alcohols, such as ethanol, isopropyl alcohol, benzyl alcohol and phenyl ethyl alcohol; glycols and glycol ethers, such as propylene glycol, hexylene glycol, ethylene glycol monomethyl, monoethyl or monobutyl ether; propylene glycol and its ethers, such as propylene glycol monomethyl ether, butylene glycol, dipropylene glycol, and also diethylene glycol alkyl ethers, such as diethylene glycol monoethyl ether and monobutyl ether; hydrocarbons such as straight chain hydrocarbons, mineral oil, polybutene, hydrogenated polyisobutene, hydrogenated polydecene, polydecene, squalene, petrolatum and isoparaffins; and mixtures thereof, to name a few.

The composition for dyeing and reducing curl and/or frizziness of hair disclosed herein may be, for example, in the form of liquids or gels that allow the hair to "stick" together and hold them in a smooth position during the leave-in time. The composition may also be in the form of a thickened cream so as to hold the hair as stiff as possible. These creams are made in the form of "heavy" emulsions, particularly, when the at least one fatty substance of the present disclosure is present in the composition, for example, glyceryl stearate, glycol stearate, self-emulsifying waxes, fatty alcohols, mineral oil and petrolatum.

The composition for dyeing and reducing curl and/or frizziness of hair has a pH greater than 7, such as from about 7.1 to about 13.5, or such as from about 7.1 to about 13, or such as from about 7.5 to about 13.

In various exemplary embodiments, the composition for dyeing and reducing curl and/or frizziness of hair is a ready-to-use composition formed by combining, in a cosmetically acceptable carrier, an alkaline composition comprising the at least one non-hydroxide base, the at least one protein denaturant and the at least one thickening agent, with a dye composition comprising at least one oxidative dye precursor and optionally, the at least one thickening agent. The alkaline composition and the dye composition can each optionally contain the at least one fatty substance and/or the at least one alkoxysilane comprising at least one solubilizing functional group. The alkaline composition has a pH greater than 7.

Adjuvants

The composition for dyeing and reducing curl and/or frizziness of hair and the neutralizing composition as disclosed herein may also each comprise at least one adjuvant chosen, for example, from silicones in soluble, dispersed and microdispersed forms, nonionic, anionic, cationic and amphoteric surfactants, suspending agents, ceramides, glycoceramides and pseudoceramides, vitamins and provitamins including panthenol, waxes other than ceramides, glycoceramides and pseudoceramides, water-soluble and liposoluble, silicone-based and non-silicone-based sunscreens, nacreous agents and opacifiers, sequestering agents, plasticizers, solubilizers, acidifying agents, mineral and organic thickeners, antioxidants, hydroxy acids, penetrating agents, fragrances, and preserving agents.

In the event that surfactants are employed in the compositions of the present invention, said compositions may be used as a shampoo. Similarly, in the event that one were to decide to use the compositions of the invention as a hair conditioner, various types of conditioning agents can be added to the composition in order to facilitate this hair treating property.

According to the present invention, there is provided a process for altering the appearance of hair, that is, for dyeing and reducing the curl and/or frizziness of hair involving the steps of: (a) providing a composition for dyeing and reducing curl and/or frizziness of hair, in a cosmetically acceptable carrier, containing at least one non-hydroxide base, at least one protein denaturant, at least one oxidative dye precursor, at least one thickening agent, optionally, at least one alkoxysilane comprising at least one solubilizing functional group; and optionally, at least one fatty substance; (b) contacting the hair with the composition for dyeing and reducing curl and/or frizziness of hair to form treated hair; (c) smoothing the treated hair using a combination of heat and means for physically smoothing hair to form smoothed hair; (d) optionally, shampooing the smoothed hair; and (e) rinsing the treated hair. The pH of the composition for dyeing and reducing curl and/or frizziness of hair is greater than 7 and the pH of the neutralizing composition is below 7.

In commercially available hair straightening or relaxing compositions, the highly caustic hydroxide compound such as sodium hydroxide must be used in order to satisfactorily straighten/relax or reduce the curl of the hair without heat. In the present invention, however, the less caustic and the lower concentrations of the non-hydroxide compound can be used because of the synergy realized by using the composition for dyeing and reducing curl and/or frizziness of hair of the present disclosure, in combination with heat and an apparatus capable of physically smoothing the hair. Without intending to be bound by theory, it is believed that a synergistic effect in hair straightening/relaxing or curl reduction is realized due to an induced supercontraction and denaturation of hair protein caused by the combination of the disclosed composition for dyeing and reducing curl and/or frizziness of hair with the heat and physical smoothing.

Moreover, due to the less caustic and the lower concentrations of the non-hydroxide compound being used, a barrier substance is not required when using the composition for dyeing and reducing curl and/or frizziness of hair of the present invention. Commercially available hair straightening/relaxing products oftentimes require the hair stylist to apply a barrier substance such as petrolatum to the skin surrounding the scalp and the area around the ears. The barrier substance is used to prevent the skin from becoming irritated if the composition contacts the skin and from staining the skin as a result of the dyes in the composition. Thus, a barrier substance is not necessary when using the process of the present invention because the concentration and the irritation of the non-hydroxide compound is much lower.

In preferred embodiments of the present disclosure, the composition for dyeing and reducing curl and/or frizziness of hair comprises, in a cosmetically acceptable carrier, at least one non-hydroxide base, at least one protein denaturant, at least one oxidative dye precursor, at least one thickening agent, at least one alkoxysilane comprising at least one solubilizing functional group, and at least one fatty substance.

In other preferred embodiments, the composition for dyeing and reducing curl and/or frizziness of hair comprises two protein denaturants, preferably chosen from urea and hydroxyethyl urea.

The contact time (processing time) of the composition for dyeing and reducing curl and/or frizziness of hair with the hair may be up to about 60 minutes, such as up to about 30 minutes, such as up to about twenty minutes. The contact tiup may also be up to about 10 minutes particularly when the process of the present disclosure is used as a maintenance regimen, i.e., as a follow up procedure to maintain the curl pattern or further reduce the curl of the hair.

The smoothing step of the present disclosure, using a combination of heat and means for physically smoothing hair to form smoothed hair, preferably includes the use of a flat iron or a blow dryer in combination with a comb, a brush, or an iron. The smoothing step of the present invention is preferably conducted at a temperature of at least 30° C.; preferably at least 50° C.; preferably at least 70° C. The heat in the smoothing step may emanate from any suitable source such as, for example, a hair dryer or blow dryer or hot/flat iron or an infrared heat generator/hair dryer in one device (e.g., Rollerball brand).

Typically, the lower the amount of non-hydroxide base present in the composition for reducing curl and/or frizziness of hair, the lower the temperature required at the smoothing step. Conversely, the amount of heat applied onto the treated hair can depend on the original hair type and/or the degree of damage to the hair.

The means for physically smoothing hair can be any apparatus capable of physically smoothing the hair such as, for example, a hair brush or comb. In one embodiment, the means for smoothing hair also serves as the source for generating heat such as, for example, a hot/flat iron.

In other embodiments of the present disclosure, the treated hair is contacted with a non-volatile oil before before or after the smoothing step. The non-volatile oil may be chosen from plant, animal, mineral and synthetic oils.

The smoothed hair may also be contacted with the neutralizing composition of the present disclosure and having a pH of below about 7 to form neutralized hair, followed by rinsing with water. The neutralizing composition may be in the form of a shampoo or a conditioner.

In some embodiments of the present disclosure, the composition for dyeing and reducing curl and/or frizziness of hair may be rinsed out from the hair before contacting the treated hair with the neutralizing composition.

Neutralizing Composition

A neutralizing composition may also be applied onto the hair after it has been smoothened using a combination of heat and means for physically smoothing hair. The neutralizing composition can comprise a cosmetically acceptable carrier chosen from water, organic solvents, and mixtures thereof. Suitable examples of cosmetically acceptable carriers include those described above.

The cosmetically acceptable carrier may, for example, be present in the neutralizing composition of the present disclosure in an amount ranging from about 0.5% to about 85% by weight, such as from about 2% to about 80% by weight, preferably from about 5 to about 70% by weight, based on the total weight of the neutralizing composition.

The neutralizing composition preferably comprises at least one oxidizing agent.

The neutralizing composition may also comprise one or more of the adjuvants listed above.

When the neutralizing composition comprising at least one oxidizing agent is applied onto the hair treated with the composition for dyeing and reducing curl and/or frizziness of hair, the color of the treated hair is altered in situ.

Oxidizing Agent

The at least one oxidizing agent of the present disclosure may be chosen from peroxides, persulfates, perborates, percarbonates, peracids, bromates, their salts and mixtures thereof. The at least one oxidizing agent may, optionally, be water-soluble.

Exemplary, non-limiting persulfates include potassium persulfate, sodium persulfate, and ammonium persulfate. In various embodiments, exemplary oxidizing agents may be chosen from sodium perborate and sodium percarbonate. In further embodiments, exemplary peracids may be chosen from organic peracids having the general formula (VIII):

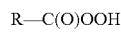

wherein, in formula (VIII), R is chosen from saturated or unsaturated, substituted or unsubstituted, straight or branched chain, alkyl, aryl or alkaryl groups having from 1 to carbon atoms. In at least some exemplary embodiments, mixtures of two or more oxidizing agents chosen from persulfates, perborates, percarbonates, peracids, perbromates, and salts thereof, may be chosen.

In various embodiments, the at least one oxidizing agent is chosen from alkali metal salts of perborates, percarbonates, perbromates, and persulfates, such as, for example, ammonium, sodium, and potassium salts.

Preferred persulfates are monopersulfates such as, for example, potassium persulfate, sodium persulfate, ammonium persulfate, as well as mixtures thereof.

The preferred oxidizing agents in the present invention are potassium persulfate, sodium persulfate and mixtures thereof.

Optional peroxides useful herein include, for example, hydrogen peroxide, magnesium peroxide, PVP-peroxide, calcium peroxide, and sodium peroxide.

The at least one oxidizing agent is present in an amount sufficient to generate color in the hair without destroying the oxidative dye precursors which have migrated into the hair prior to completion of the hair dyeing process to the desired color/shade.

Preferably, the at least one oxidizing agent is provided in the neutralizing composition comprising a cosmetically acceptable carrier as described above.

In general, the at least one oxidizing agent will be present in the neutralizing composition of the present disclosure in an amount of at least 1% by weight, based on the total weight of the neutralizing composition.

According to a preferred embodiment, the at least one oxidizing agent is present in the neutralizing composition of the present disclosure in an amount ranging from about 1% by weight to about 80% by weight, preferably from about 5% by weight to about 75% by weight, based on the total weight of the neutralizing composition.

The pH of the neutralizing composition can be from about 1 to about 6.5, such as from about 2 to about 6, or such as from about 2 to about 5, or such as at about 3, or at about 4, or at about 4.8, or at about 5, and it may be adjusted to the desired value using pH adjusting agents that are well known in the art in the dyeing of keratin fibers.

According to a preferred embodiment of the invention, the neutralizing composition is substantially anhydrous.

The term "substantially anhydrous" means that the neutralizing composition is either completely free of water or contains no appreciable amount of water, preferably no more than 1% by weight, and more preferably no more than 0.5% by weight, based on the weight of the neutralizing composition.

According to a particularly preferred embodiment of the invention, the neutralizing composition is totally anhydrous, that is to say it does not contain water at all.

When the neutralizing composition is substantially anhydrous or totally anhydrous, the cosmetically acceptable carrier is chosen from organic solvents.

The neutralizing composition of the present disclosure may also contain at least one fatty substance and/or at least one thickening agent as described above.

In some embodiments of the present disclosure, the neutralizing composition will additionally contain an oxidizing agent chosen from peroxides and its salts. Peroxides useful herein include, for example, hydrogen peroxide, magnesium peroxide, PVP-peroxide, calcium peroxide, and sodium peroxide.

The neutralizing composition may be in the form of a powder, gel, liquid, foam, lotion, cream, mousse, and emulsion.

It should be noted that the use of a catalyst during the oxidation of the oxidative dye precursor such as, for example, cupric or ferrous salt, is not necessary in order to achieve a desired color/shade.

Thus, according to a preferred embodiment of the present disclosure, the composition for dyeing and reducing curl and/or frizziness of hair and the neutralizing composition of the present disclosure are substantially free of an oxidation catalyst, i.e., such catalyst is present in a less than catalytically effective amount in the hair treatment and neutralizing compositions.

As used herein, "oxidation catalyst" refers to transition metal cations that can aid in the oxidation of certain dye precursors, such as cupric and ferrous ions.

According to a particularly preferred embodiment, the composition for dyeing and reducing curl and/or frizziness of hair and the neutralizing composition are each totally free of cupric ions and of ferrous ions.

According to a particularly preferred embodiment, the composition for dyeing and reducing curl and/or frizziness of hair and the neutralizing composition do not contain hydrogen peroxide.

According to some embodiments, when the oxidative dye precursor employed in the composition for dyeing and reducing curl and/or frizziness of hair is an auto-oxidizable compound, i.e., the color development occurs in the presence of air, the neutralizing composition may not require an oxidizing agent as described above.

According to other embodiments, the composition for dyeing and reducing curl and/or frizziness of hair and/or neutralizing composition do not contain more than about 2.5% by weight of aqueous ammonia based on the total weight of the composition for dyeing and reducing curl and/or frizziness of hair and/or neutralizing composition.

The neutralizing composition is applied onto the hair for a period of time sufficient to neutralize the pH on the hair and/or develop color, in situ, to form colored hair. In general, the neutralizing composition is applied onto the hair for a period of from 1 to t 20 minutes, such as from 1 to 10 minutes, for example from 1 to 5 minutes.

In various exemplary embodiments, the neutralizing composition is formed by combining a surfactant-based composition containing at least one surfactant, such as a shampoo, with a oxidizer composition containing at least one oxidizing agent. Preferably, the oxidizer composition containing the at least one oxidizing agent is an anhydrous composition.

In one embodiment of the present disclosure, an anhydrous oxidizer composition and a shampoo composition are provided and are combined immediately prior to use, to form the neutralizing composition wherein the oxidizer composition contains at least one oxidizing agent chosen from persulfates, perborates, percarbonates, bromates, peroxides, their salts, and mixtures thereof and the shampoo composition contains a cosmetically acceptable carrier and at least 4% by weight, based on the total weight of the shampoo composition, of at least one surfactant chosen from anionic, amphoteric, nonionic, zwitterionic, cationic surfactants, and mixtures thereof. The resulting neutralizing composition contains from about 1% to about 80% by weight of the oxidizing agent, based on the total weight of the neutralizing composition. Optionally, the hair may also first be contacted with a pre-alkalizing composition having a pH of from about 8.0 to about 12.0 to form pre-alkalized hair prior to application of the dyeing and curl/frizziness reducing composition. This pre-alkalizing step renders the process for reducing the curl and/or frizziness of hair more efficient and less time-consuming.

The pre-alkalizing step comprises contacting the hair with a pre-alkalizing composition which may be provided in any suitable form. Examples thereof include, but are not limited to, a shampoo, a conditioner or an alkaline solution in general. In a particularly preferred embodiment, the alkaline composition is in the form of a shampoo which would facilitate both the pre-alkalizing and cleaning of the hair at the same time.

Thus, in one embodiment of the present invention, there is provided a process for dyeing and reducing curl and/or frizziness of hair that includes first pre-alkalizing or treating the hair with the alkaline composition before contacting the hair with the dyeing and curl/frizziness reducing composition to form treated hair. Preferably, the alkaline composition is rinsed from the hair and the hair is dried, blown dry, prior to contacting the hair with the dyeing and curl/frizziness reducing composition.

The pH of the pre-alkalizing composition can range from above 7 to about 12, such as from about 7.5 to 12, or such as from about 7.5 to about 10 or such as from about 8 to about 12 or such as from about 8 to about 10.

Due to the less caustic and the lower concentrations of the non-hydroxide compound being used, a barrier substance is not required when using the composition for dyeing and reducing curl and/or frizziness of hair. Commercially available hair relaxing products oftentimes require the hair stylist to apply a barrier substance such as petrolatum to the skin surrounding the scalp and the area around the ears. The barrier substance is used to prevent the skin from becoming irritated if the hair relaxing product contacts the skin. Thus, a barrier substance is not necessary when using the process of the present invention because the concentration and therefore, the degree of irritation of the non-hydroxide compound, are much lower.

The present invention will be better understood from the examples which follow, all of which are intended for illustrative purposes only, and are not meant to unduly limit the scope of the invention in any way.

EXAMPLES

Example 1

Dyeing and Curl Reduction with the Inventive Hair Treatment Formula (Clear Gel Composition)

| Ingredient | test formula % by weight |
|---|---|
| SODIUM SULFITE | 0.4 |
| ASCORBIC ACID | 0.3 |
| DISODIUM EDTA | 0.1 |
| XANTHAN GUM | 2 |
| MONOETHANOLAMINE | 1 |
| PENTASODIUM PENTETATE | 2 |
| SODIUM METASILICATE | 2 |
| CETEARYL ALCOHOL (and) DIPALMITOYLETHYL HYDROXYETHYLMONIUM METHOSULFATE | 3 |
| COCO-GLUCOSIDE | 2 |
| RESORCINOL | 0.6 |
| p-PHENYLENEDIAMINE | 0.58 |
| UREA | 10 |
| HYDROXYETHYL UREA | 2 |
| WATER | Q.S. |

| Surfactant-based composition (shampoo) | |
|---|---|
| Ingredient | % by weight |
| SODIUM LAURETH SULFATE | 13.85 |
| DISODIUM COCOAMPHODIACETATE | 10 |
| AMMONIUM HYDROXIDE | 3.2 |
| TARTARIC ACID | 0.1 |
| CITRIC ACID | 4 |
| FRAGRANCE | 0.3 |
| POLYQUATERNIUM-10 | 0.8 |
| SALICYLIC ACID | 0.45 |
| BENZOIC ACID | 0.45 |
| HEXYLENE GLYCOL | 1 |
| ETHYLHEXYL METHOXYCINNAMATE | 0.05 |
| PEG-60 HYDROGENATED CASTOR OIL | 0.5 |
| TOCOPHERYL ACETATE | 0.05 |
| WATER | Q.S. |

| Oxidizing composition | |
|---|---|
| Ingredient | % by weight |
| SODIUM PERSULFATE | 75 |
| EDTA | 1 |
| SILICA | 2.3 |
| ZEA MAYS (CORN) STARCH | 20 |
| HYDROGENATED POLYDECENE | 1.7 |

Two hair swatches, each a different type of hair [permed, and natural wavy (loose curls)] were treated according to the following procedure:

Thirty (30) grams of the composition above was applied to each hair swatch. The composition was left on the swatches for 50 minutes, after which heat (using a flat iron) was applied to the treated hair to straighten/reduce the curl of the hair. The swatches were then treated with a neutralizing composition formed by combining the shampoo composition and the oxidizing composition (92%:8% by weight). The pH of the neutralizing composition was at about 4.8. The neutralizing composition was allowed to remain on the swatches for 5 minutes. The swatches were then washed and dried. The permed hair was used as a control to validate that the hair fibers were colored according to the desired shade.

Natural wavy hair as used herein refers to curly hair (curl type III) whose degree of curl is in between straight hair and kinky hair which has very tight curls (curl type V).

It was found that the process above dyed the swatches with the desired color/shade and significantly reduced the curl on the natural wavy hair.

Example 2

Retention of Color and Retention of Curl Reduction Study

The color fading and curl reducing properties of the composition in Example 1 were studied on three different types of hair: permed, African American (kinky hair with very tight curls), and natural wavy hair. The swatches were treated according to the procedure above. The permed hair was used as a control to validate that the hair fibers were colored according to the desired shade. It was found that the curl on the African American hair was significantly reduced and the natural wavy hair was straightened.

Each swatch was then subjected to 5 cycles of shampooing, with each cycle involving treating each swatch with 5 grams of shampoo and rinsing with water.

After the five cycles of shampooing and rinsing, it was found that the color on the swatches did not fade and in fact appeared darker (probably due to a continued color development). In addition, the curl on the African American hair was still significantly reduced or loosened, and the wavy hair remained straight.

Example 3

Lift Study

The level of lightening (lift) of the color of hair was studied on swatches of four different types of hair: permed, unpermed, Asian hair (natural dark color) and natural wavy hair (medium brown shade) using three inventive composition for dyeing and reducing curl and/or frizziness of hairs and a control formula. The swatches were treated according to the procedure in Example 1.

| Ingredients | Test formula A % by weight | Test formula B % by weight | Test formula C % by weight |
|---|---|---|---|
| SODIUM SULFITE | 0.4 | 0.4 | 0.4 |
| ASCORBIC ACID | 0.3 | 0.3 | 0.3 |
| DISODIUM EDTA | 0.1 | 0.1 | 0.1 |
| XANTHAN GUM | 2 | 2 | 2 |
| MONOETHANOLAMINE | 1 | 1 | 1 |
| PENTASODIUM PENTETATE | 2 | 2 | 2 |
| SODIUM METASILICATE | 2 | | |
| ARGININE | | | 5 |
| SODIUM HYDROXIDE | | 2.1 | |
| CETEARYL ALCOHOL (and) DIPALMITOYLETHYL HYDROXYETHYLMONIUM METHOSULFATE | 3 | 3 | 3 |
| COCO-GLUCOSIDE | 2 | 2 | 2 |
| UREA | 10 | 10 | 10 |
| HYDROXYETHYL UREA | 2 | 2 | 2 |
| WATER | Q.S. | Q.S. | Q.S. |

The test formulas lifted the color of the natural wavy hair by one level as compared to 3 levels of lift caused by a standard permanent oxidative dye formula containing 7.41% ammonium hydroxide (aqueous ammonia) in the same type of hair. On the other hand, the test formulas did not noticeably lift the color of the Asian hair while 2 levels of lift were observed using the standard dye formula. The standard dye formula was able to lift color to a higher level in the same type of hair because it contained 18% sodium hydroxide, whereas the test formulas contained no or very little amount of sodium hydroxide (not more than about 2.1% by weight).

Significant reductions in curl were observed for the African American and the natural wavy hair treated with the test formulas. It was also observed that the various hair types treated with test formula C, which contained arginine, felt more conditioned to the touch as compared to the hair treated with the other test formulas and with the control formula.

Example 4

Study on Thickening Agents

The effect of the presence of thickening agents was tested as shown below.

| Ingredients | Test formula D % by weight | Test formula E % by weight | Test formula F % by weight |
|---|---|---|---|
| WATER | Q.S. | Q.S. | Q.S. |
| TRIETHANOLAMINE | 0.1 | 0.2 | 0.2 |
| ETHANOLAMINE | 1 | 1 | 1 |
| HEXYLENE GLYCOL | 2 | 2 | 2 |
| UREA | 10 | 10 | 10 |
| HYDROXYETHYL UREA | 5 | 5 | 5 |
| DISODIUM EDTA | 0.2 | 0.2 | 0.2 |
| ASCORBIC ACID | 0.3 | 0.3 | 0.3 |
| SODIUM SULFITE | 0.4 | 0.4 | 0.4 |
| p-PHENYLENEDIAMINE | 0.54 | 0.54 | 0.54 |
| p-AMINOPHENOL (and) SODIUM METABISULFITE | 0.62 | 0.62 | 0.62 |
| 2-METHYL-5-HYDROXYETHYLAMINOPHENOL | 0.8 | 0.8 | 0.8 |
| 4-AMINO-2-HYDROXYTOLUENE | 0.86 | 0.86 | 0.86 |
| 6-HYDROXYINDOLE | 0.06 | 0.06 | 0.06 |
| CARBOMER (THICKENING AGENT) | | 0.2 | |
| XANTHAN GUM (THICKENING AGENT) | | | 2 |

It was observed that the dyes in test formula D which did not contain a thickening agent precipitated to the bottom for lack of viscosity and solubility in the base while the gel structure in test formula E which contained a thickening agent comprising a charged compound, carbomer, fell apart as soon as the dyes were added to the gel. On the other hand, the gel structure of test Formula F, which contained xanthan gum, a nonionic thickening agent, remained stable when the dyes were added.

Example 5

Study on Red Shades

The next test was to study the effect of APTES and to determine whether hair can be effectively colored a red shade. The hair was treated according to the procedure in Example 1.

| Ingredients | Test formula G % by weight |
|---|---|
| WATER | Q.S. |
| XANTHAN GUM | 2 |
| TRIETHANOLAMINE | 0.2 |
| ETHANOLAMINE | 1 |
| HEXYLENE GLYCOL | 2 |
| UREA | 10 |
| HYDROXYETHYL UREA | 5 |
| AMINOPROPYL TRIETHOXYSILANE (APTES) | 1 |
| DISODIUM EDTA | 0.2 |
| ASCORBIC ACID | 0.3 |
| SODIUM SULFITE | 0.4 |
| m-AMINOPHENOL | 0.25 |
| 1-HYDROXYETHYL 4,5-DIAMINO PYRAZOLE SULFATE (provides the red color) | 0.5 |

With respect to conditioning, it was observed that the hair treated with the test formula G containing APTES imparted more conditioning to the hair compared to test formula F in Example 4 which did not contain APTES.

In addition, it was observed that the hair was effectively colored a red color.

Example 6

Curl Reduction/Straightening Study, Color Deposition Study and Rinsing Study Involving an Additional Rinsing Step Before the Application of the Neutralizing Composition onto the Hair The inventive formulas below were tested against a standard permanent oxidative dye formulas (standard dye formulas) containing high amounts of ammonium hydroxide (aqueous ammonia) on swatches of two types of hair: permed and natural wavy hair. For the tests, 2 grams of product per gram of hair were used. The swatches were treated with the test formulas for 20 minutes then heat was applied to the swatches (4 passes with the flat iron).

In order to investigate the effects of rinsing the hair with water before and after applying the neutralizing composition, one of the swatches was rinsed before and another was rinsed after the application. The neutralizing composition was left on the hair for 2 minutes for test formulas H and I, and 5 minutes for test formulas J and K. The swatches were then hung to dry.

| Ingredients | Test formula H Red shade % By weight | Test formula I Red shade % By weight | Test formula J Brown shade % By weight | Test formula K Brown shade % By weight |
|---|---|---|---|---|
| WATER | QS | QS | QS | QS |
| XANTHAN GUM | 2 | 2 | 2 | 2 |
| TRIETHANOLAMINE | 0.2 | 0.2 | 0.2 | 0.2 |
| MONOETHANOLAMINE | 1 | 1 | 1 | 1 |
| HEXYLENE GLYCOL | 2 | 2 | 2 | 2 |
| UREA | 10 | 10 | 10 | 10 |
| AMINOPROPYL TRIETHOXYSILANE | 1 | — | 1 | — |
| DISODIUM EDTA | 0.2 | 0.2 | 0.2 | 0.2 |
| ASCORBIC ACID | 0.3 | 0.3 | 0.3 | 0.3 |
| SODIUM SULFITE | 0.4 | 0.4 | 0.4 | 0.4 |

-continued

| Ingredients | Test formula H Red shade % By weight | Test formula I Red shade % By weight | Test formula J Brown shade % By weight | Test formula K Brown shade % By weight |
|---|---|---|---|---|
| m-AMINOPHENOL | 0.25 | 0.25 | 0.6 | 0.6 |
| 1-HYDROXYETHYL 4,5-DIAMINO PYRAZOLE SULFATE | 0.5 | 0.5 | | |
| 1,4-DIAMINO-BENZENE | | | 0.58 | 0.58 |

Example 6a

Color Deposition Study for Red Shades and Rinsing Step Study Involving an Additional Rinsing Step Before the Application of the Neutralizing Composition onto the Hair The color of the hair swatches treated with test formulas H and I and hair swatches treated with a standard dye formula for red shades containing 18% ammonium hydroxide (aqueous ammonia) was measured using a Minolta CM2002 colorimeter in the L*a*b* system. In the L*a*b* system, the 3 parameters denote, respectively, the intensity or lightness of the color (L*), the value of the color on a green/red axis (a*) and the value of the color on a blue/yellow axis (b*). According to this system, the greater the value of L, the lighter or less intense the color. Conversely, the lower the value of L, the darker or more intense the color. Also, according to this system, the overall color change, ΔE, can be calculated from the ΔL, ΔA, and ΔB values. The hair used as a control was 90% grey permed hair.

Colorimetric Results

| Treatment of hair | L* | a* | b* | $\Delta E_1$ (difference between treated and untreated hair) |
|---|---|---|---|---|
| No treatment - untreated swatch; 90% permed gray hair (control) | 62.3 | 1.16 | 13.24 | |
| standard dye formula for red shade* | 22.55 | 20 | 9.5 | 44.15 |
| Test formula H with rinsing before Neutralization | 41.45 | 16.13 | 3.52 | 27.45 |
| Test formula H without rinsing before Neutralization | 32.62 | 20.69 | 1.85 | 37.31 |
| Test formula I with rinsing before Neutralization | 37.17 | 19.33 | 2.18 | 32.92 |
| Test formula I without rinsing before Neutralization | 33.53 | 22.34 | 2.1 | 37.42 |

*contained oxidative dyes ammonium thiolactate, pentasodim pentetate, propylene glycol, glycol distearate, fatty alcohols, fatty acid, cationic agents, silica dimethyl silylate, thickening agent, nonionic surfactants, 1.15% by weight monoethanolamine, 18% by weight aqueous ammonia and water The a values among the hair swatches treated with the standard hair color for red shade and the test formulas H and I were comparable and were significantly greater than the a value for the untreated swatch. This indicates that the test formulas were able to effect a color change on the hair. In addition, the hair treated with the test formulas demonstrated significant overall color changes, $\Delta E_1$, between the untreated and the treated hair. Although the hair treated with the standard hair color exhibited a higher color change, this could be attributed to the presence of 18% ammonium hydroxide (aqueous ammonia) in the formula. These results indicate good color deposit using the test formulas and that the hair swatches were effectively dyed a red shade even without the presence of aqueous ammonia. These results were also visually observed.

As for the effect of rinsing, the comparable overall color changes or differences between the hair treated with the test formulas and the untreated hair indicate that the additional step of rinsing before applying the neutralizing composition onto the smoothed hair did not affect the degree of color deposit on the hair treated with the test formulas. These results were also visually observed. Therefore, the hair may be rinsed before applying the neutralizing composition without compromising the color development on the hair.

In addition, the swatches treated with the formulas containing the alkoxysilane felt more conditioned to the touch.

Example 6b

Color Deposition Study for Brown Shades and Rinsing Step Study (Rinsing Employed Before Application of the Neutralizing Composition Versus after Application of the Neutralizing Composition A colorimetric study comparing test formulas J and K above with a standard permanent oxidative dye formula (standard dye formula) for brown shade containing 10% ammonium hydroxide (aqueous ammonia). The colorimetric measurements were made as described above.

Colorimetric Results

| Treatment | L* | a* | b* | $\Delta E_3$ (treated versus untreated hair) |
|---|---|---|---|---|
| untreated swatch; 90% permed gray hair (control) | 62.3 | 1.16 | 13.24 | |
| standard dye formula for brown shade* | 32.19 | 2.99 | 9.88 | 30.35 |

| Treatment | L* | a* | b* | ΔE₃ (treated versus untreated hair) |
| --- | --- | --- | --- | --- |
| Test formula J with rinsing before Neutralization | 20.54 | 3.36 | 2.47 | 43.18 |
| Test formula J without rinsing before Neutralization | 20.1 | 1.57 | 2.46 | 43.56 |
| Test formula K with rinsing before Neutralization | 20.58 | 2.72 | 1.78 | 43.29 |
| Test formula K without rinsing before Neutralization | 18 | 1.74 | 1.29 | 45.89 |

*contained oxidative dyes, ammonium thiolactate, sodium sulfite/metabisulfite, silica dimethyl silylate, propylene glycol, glycerin, fatty alcohols, fatty acids, alkoxylated fatty amine, thickening agents, cationic agents, chelants, amphoteric surfactants, 6% by weight steararmide and monoethanolamine, 1.21% by weight monoethanolamine, 10% by weight aqueous ammonia and water The L values (more representative parameter for the brown shade to determine adequate color deposit) among the hair swatches treated with the standard dye formula and the test formulas J and K were comparable and were lighter than the L value for the untreated swatch. This indicates that the test formulas were able to effect a color change on the hair. In addition, the hair treated with the test formulas demonstrated significant overall color changes, $\Delta E_3$, between the untreated and the treated hair while the hair treated with the standard dye formula, which contained 10% ammonium hydroxide, exhibited less color change. These results indicate good color deposit using the test formulas and that the hair swatches were effectively dyed a brown shade even without the presence of aqueous ammonia. These results were also visually observed.

As for the effect of rinsing, the comparable overall color changes even with the rinsing step before applying the neutralizing composition indicate that this additional step does not affect the degree of color deposit on the hair treated with the test formulas. These results were also visually observed. Therefore, the hair may also be rinsed before applying the neutralizing composition without compromising the color development on the hair.

Study on curl and frizziness reduction using test formula K on the natural wavy hair according to the procedure in Example 1

| Length before treatment | Length after treatment | Width* at 7 cm** before treatment | Width* at 7 cm** after treatment | Width* at 10 cm** before treatment | Width* at 10 cm** after treatment |
| --- | --- | --- | --- | --- | --- |
| 14.5 | 16.25 | 3 | 2.5 | 5.5 | 3.5 |

*Width was measured across the swatch to determine reduction in frizz or volume of the hair
**measured at the specified distance from the root end The results in the table above show that the natural wavy hair was longer and the frizz or volume of the hair was reduced after the hair was treated with the test formula.

Example 7

Curl Reduction and Frizz Control Study

Hair Swatches: Bleached hair swatches (~1.3 g of hair per swatch) were prepared from samples of Natural wavy hair type. Two hair swatches were assigned as test swatches and one swatch was assigned as a control (no treatment).

Step 1: The test and control hair swatches were cleansed with a shampoo (0.52 grams shampoo per swatch) and simultaneously washed with tap water for 2 minutes at 30° C. and combed in order to detangle the hair. The test hair swatches were then blow dried and pulled straight at the same time.

Step 2: Each test hair swatch was treated with about 4 grams of the invention's composition for dyeing and reducing curl and/or frizziness of hair (inventive formula K in example 6 above). The composition was combed through the hair and allowed to remain on the test hair swatches for about 20 minutes at 45° C. Each treated test hair swatch was then smoothened by passing a titanium flat iron 3 times through each swatch, 5 seconds per pass, at 370° F.

Step 3—Each test swatch was treated with about 1.3 grams of the invention's neutralizing composition (1:1 ratio of neutralizing composition to weight of hair swatch) by combing it through the hair. The neutralizing composition was allowed to remain on the hair for about 5 minutes.

The test and control hair swatches were then cleansed with a shampoo (0.52 grams shampoo per swatch) and simultaneously washed with tap water for 2 minutes at 30° C. and combed in order to detangle the hair. The swatches were combed 3 times before hanging to air dry. After drying, digital photographs of the test and control hair swatches were taken against a ruler in order to compare the length and width of the swatches with the control swatch.

In order to determine the durability of the curl and/or frizz reduction effect and the artificial color on the hair, one test hair swatch and one control swatch were each shampooed/washed/combed for 10 cycles, with hanging to air dry in between each cycle. Digital photographs of the swatches were taken every 2 cycles.

The photographs of the hair swatches showed that the test hair swatches appeared longer and significantly more straight than the control swatch. In addition, the test hair swatches were significantly less frizzy as seen from the smaller width of the test hair swatch as compared to the width of the control swatch.

Example 8

Anti-Frizz Study

| Treatment | Length of swatch, cm | Width of swatch at midpoint of length of swatch, cm | Width at the end of the swatch, cm |
| --- | --- | --- | --- |
| Untreated natural wavy hair | 16 | 3.1 | 6.8 |
| Hair treated with test formula K | 17 | 2.1 | 4.4 |

The measurements above of the length of the hair swatches show that the swatch treated with the test formula was longer compared to the untreated hair which indicates that the hair was straightened. In addition, the width of the treated swatches at midpoint and at the ends are less than that of the untreated swatch which indicates that the treated hair was less frizzy or spread out compared to the untreated hair.

Example 9

Test Formula Containing a Fatty Substance (Mineral Oil)

| INCI US | 87928 MX |
|---|---|
| UREA | 10 |
| DISODIUM EDTA | 0.2 |
| MONOETHANOLAMINE | 4.4 |
| SODIUM SULFITE | 0.4 |
| HYDROXYETHYL UREA | 5 |
| m-AMINOPHENOL | 0.25 |
| 1-HYDROXYETHYL 4,5-DIAMINO PYRAZOLE SULFATE | 0.5 |
| MINERAL OIL | 60 |
| CETEARYL ALCOHOL | 2.5 |
| CARBOMER | 0.4 |
| AMINOPROPYL TRIETHOXYSILANE | 1 |
| WATER | 11.05 |
| SODIUM CETEARYL SULFATE | 2 |
| STEARETH-20 | 2 |
| ASCORBIC ACID | 0.3 |

Example 10

Study on Retention of Curl Reduction and Frizz/Volume Reduction or Control on Natural Wavy Hair and Retention of Color on Permed Hair after Multiple Washings

| Length before treatment, cm | 13 |
|---|---|
| Length after 10 washes, cm | 14 |
| Length after 20 washes, cm | 15.5 |
| Width* at 7 cm** before treatment | 2.5 |
| Width* at 7 cm** after 10 washes | 2 |
| Width* at 7 cm** after 20 washes | 2.5 |
| Width* at 10 cm** before treatment | 4 |
| Width* at 10 cm** after 10 washes | 2 |
| Width* at 10 cm** after 20 washes | 3.5 |

*Width was measured across the swatch to determine reduction in frizz or volume of the hair
**measured at the specified distance from the root end Natural wavy hair and permed hair were treated with the test formula K according to the procedure in Example 1. The hair was then subjected to 20 shampoo/rinse cycles (washes) which corresponds to a period of about 4 to about 6 weeks that a consumer would wait until the next coloration/hair treatment.

The length and width measurements in the table above show that treatment on the natural wavy hair provided excellent retention of curl reduction (the hair did not revert to its original curl length) and good frizz/volume control even after the $10^{th}$ and $20^{th}$ washes. At the $10^{th}$ wash, the widths along the length of the swatch were still less than the widths before the treatment. At the $20^{th}$ wash, the widths along the length of the swatch were comparable to or less than the widths before the treatment. This indicates long lasting retention of curl reduction and frizz/volume control even after multiple washing cycles.

From a visual assessment of the color of the permed hair, it was observed that the treatment resulted in excellent color retention even after the $10^{th}$ and $20^{th}$ wash cycles.

It is to be understood that the foregoing describes preferred embodiments of the invention and that modifications may be made therein without departing from the spirit or scope of the invention as set forth in the claims.

What is claimed is:

1. A process for altering the appearance of hair, the process comprising:
    (a) providing a composition for dyeing and reducing curl and/or frizziness of hair, said comprising, in a cosmetically acceptable carrier:
        (i) at least one non-hydroxide base;
        (ii) at least one protein denaturant different from (a)(i);
        (iii) at least one oxidative dye precursor;
        (iv) at least one thickening agent;
        (v) optionally, at least one alkoxysilane comprising at least one solubilizing functional group; and
        (vi) optionally, at least one fatty substance;
    (b) contacting the hair with the composition in (a) to form treated hair;
    (c) smoothing the treated hair using a combination of heat and means for physically smoothing hair to form smoothed hair;
    (d) optionally, shampooing the smoothed hair; and
    (e) rinsing the treated hair.

2. The process of claim 1, wherein the composition for dyeing and reducing curl and/or frizziness of hair is a ready-to-use composition.

3. The process of claim 1, wherein (a)(i) is chosen from an alkylamine, alkyleneamine, alkanolamine, aminomethylpropanol, basic amino acids and mixtures thereof.

4. The process of claim 1, wherein (a)(i) is chosen from ethylenediamine, monoethanolamine, triethanolamine, and mixtures thereof.

5. The process of claim 1, wherein (a)(i) is chosen from arginine, lysine, histidine and mixtures thereof.

6. The process of claim 1, wherein (a)(i) is chosen from an alkali metal phosphate, an alkali metal carbonate, and mixtures thereof.

7. The process of claim 1, wherein (a)(i) is employed in an amount of from about 0.1% to about 50% by weight, based on the weight of the composition in (a).

8. The process of claim 1, wherein (a)(i) is employed in an amount of from about 1% to about 5% by weight, based on the weight of the composition in (a).

9. The process of claim 1, wherein (a)(ii) is chosen from urea, guanidine, urea derivatives and/or salts, guanidine derivatives and/or salts, and mixtures thereof.

10. The process of claim 1, wherein (a)(ii) is chosen from urea, hydroxyethyl urea and mixtures thereof.

11. The process of claim 1, wherein (a)(ii) is employed in an amount of from about 0.1% to about 50% by weight, based on the weight of the composition in (a).

12. The process of claim 1, wherein (a)(ii) is employed in an amount of from about 2% to about 20% by weight, based on the weight of the composition in (a).

13. The process of claim 1, wherein (a)(ii) is chosen from urea, hydroxyethyl urea and mixtures thereof.

14. The process of claim 1, wherein (a)(ii) comprises at least two protein denaturants present in a ratio by weight ranging from about 10:1 to about 1:10.

15. The process of claim 1, wherein (a)(iii) is chosen from oxidation bases and couplers, and mixtures thereof.

16. The process of claim 1, wherein (a)(iii) is chosen from ortho- and para-phenylenediamine oxidation bases, double bases, ortho- and para-aminophenols, heterocyclic bases, as well as salts of addition of these compounds with an acid and meta-aminophenol, meta-phenylenediamine, meta-diphenol, naphthol couplers, heterocyclic couplers and acid salts thereof.

17. The process of claim 1, wherein (a)(iv) is chosen from gums, waxes, silica gels, polysaccharides, clays, silicas, fatty acid soaps, fatty acid alkanolamides, poly(acrylic acid)s, esters of polyethylene glycol, crosslinked copolymers of acrylamide and of a monomer selected from the group consisting of ammonium acrylate, 2-acrylamido-2-methylpropanesulfonic acid and methacryloyloxyethyltrimethylammonium chloride, polyurethanes, and crosslinked methyl vinyl ether-maleic acid copolymers.

18. The process of claim 1, wherein (a)(iv) is chosen from xanthan gum and guar gum.

19. The process of claim 1, wherein (a)(iv) is present in an amount of from about 1% to about 10% by weight, based on the weight of the composition in (a).

20. The process of claim 1, wherein (a)(v) is 3-aminopropyltriethoxysilane.

21. The process of claim 1, wherein (a)(v) is employed in an amount of from about 1% to about 10% by weight, based on the weight of the composition in (a).

22. The process of claim 1, wherein (a)(vi) is chosen from lower alkanes, fatty alcohols, fatty acids, esters of fatty acids, esters of fatty alcohol, non-silicone oils, non-silicone waxes and silicones.

23. The process of claim 1, wherein (a)(vi) is present in an amount of at least about 10% by weight, based on the weight of the composition in (a).

24. The process of claim 1, wherein the composition in (a) further comprises at least one direct dye.

25. The process of claim 1, wherein (b) is performed for less than about 60 minutes.

26. The process of claim 1, wherein the means for physically smoothing hair in (c) is chosen from a brush, a comb, and an iron.

27. The process of claim 1, wherein (c) is performed using a hot/flat iron at a temperature of at least about 70° C.

28. The process of claim 1, wherein the treated hair is rinsed or washed after step (b).

29. The process of claim 1, wherein the process further comprises contacting the hair with a conditioning agent chosen from plant oils, synthetic oils, silicones, esters, humectants, conditioning polymers, and cationic agents prior to (c) or (d) or (e) or after step (e).

30. The process of claim 1, further comprising contacting the smoothed hair with a neutralizing composition after step (c) to form neutralized hair wherein the neutralizing composition has a pH of below about 7.

31. The process of claim 30, wherein the neutralizing composition comprises at least one oxidizing agent chosen from persulfates, perborates, percarbonates, peroxyacids, bromates, peroxides, their salts and mixtures thereof.

32. The process of claim 30, wherein the neutralizing composition comprises at least one oxidizing agent chosen from persulfate salts and mixtures thereof.

33. The process of claim 32, wherein the at least one oxidizing agent is present in an amount of at least about 1% by weight, based on the weight of the neutralizing composition.

34. The process of claim 32, wherein the neutralizing composition is applied onto the smoothed hair in order to alter the color of the hair in situ.

35. The process of claim 31, wherein the neutralizing composition is substantially anhydrous.

36. The process of claim 30, wherein the neutralizing composition comprises, in a cosmetically acceptable carrier, at least one surfactant chosen from anionic, amphoteric, nonionic and cationic surfactants.

37. The process of claim 30, wherein the pH of the neutralizing composition is from about 1 to about 6.

38. The process of claim 30, wherein the smoothed hair is rinsed prior to contacting the smoothed hair with the neutralizing composition.

39. The process of claim 1, wherein the composition in (a) is substantially free of formaldehyde-generating compounds.

40. The process of claim 1, wherein the composition in (a) does not contain more than about 2.5% by weight of aqueous ammonia based on the total weight of the composition in (a).

41. The process of claim 1, wherein the composition in (a) comprises an alkaline composition containing, in a cosmetically acceptable carrier, at least one non-hydroxide base and at least one protein denaturant different from the at least one non-hydroxide base.

42. The process of claim 1, wherein the composition in (a) comprises a dye composition containing, in a cosmetically acceptable carrier, at least one oxidative dye precursor.

43. A kit for dyeing and reducing the curl and/or frizziness of hair, the kit comprising:
1) a first unit containing, in a cosmetically acceptable carrier:
   (a) at least one non-hydroxide base;
   (b) at least one protein denaturant different from (a);
   (c) at least one dye chosen from oxidative dye precursors; and
   (d) at least one thickening agent;
   (e) optionally, at least one alkoxysilane comprising at least one solubilizing functional group; and
   (f) optionally, at least one fatty substance; and
2) a second unit containing:
   (a) at least one oxidizing agent chosen from persulfates, perborates, percarbonates, peroxyacids, bromates, peroxides, their salts and mixtures thereof; and
   (b) optionally, at least one fatty substance.

44. The kit of claim 43, further comprising a third unit containing, in a cosmetically acceptable carrier, at least one anionic surfactant.

45. A composition for dyeing and reducing curl and/or frizziness of hair, said composition comprising, in a cosmetically acceptable carrier:
   (a) from about 1 to about 5% by weight of at least one non-hydroxide base chosen from monoethanolamine and triethanolamine;
   (b) from about 2 to about 20% by weight of a protein denaturant comprising urea and hydroxyethylurea present in a ratio by weight ranging from about 5:1 to about 2:1;
   (c) at least one dye chosen from oxidative dye precursors;
   (d) at least one thickening agent chosen from xanthan gum and guar gum;
   (e) from about 1 to about 10% by weight of at least one alkoxysilane comprising at least one solubilizing functional group; and
   (f) at least one fatty substance in an amount of at least 10% by weight;
wherein all weights are based on the weight of the composition.

* * * * *